United States Patent
Okamura et al.

(10) Patent No.: US 6,277,598 B1
(45) Date of Patent: *Aug. 21, 2001

(54) DNA MOLECULE ENCODING INTERFERON-GAMMA (IFN-λ) INDUCING FACTOR (IGIF, IL-18) AND DNA FRAGMENT THEREOF

(75) Inventors: Haruki Okamura, Osaka; Tadao Tanimoto, Okayama; Kakuji Torigoe, Okayama; Toshio Kunikata, Okayama; Mutsuko Taniguchi, Okayama; Keizo Kohno, Okayama; Masashi Kurimoto, Okayama, all of (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/251,911

(22) Filed: Feb. 19, 1999

Related U.S. Application Data

(60) Continuation of application No. 08/908,005, filed on Aug. 11, 1997, now Pat. No. 5,914,253, which is a division of application No. 08/502,535, filed on Jul. 14, 1995, now Pat. No. 5,912,324.

(30) Foreign Application Priority Data

Jul. 14, 1994 (JP) .................................................. 6-184162
Feb. 10, 1995 (JP) .................................................. 7-045057

(51) Int. Cl.[7] ............................ C12N 15/24; C07K 14/54
(52) U.S. Cl. ................. 435/69.52; 435/69.5; 435/320.1; 435/252.3; 435/325; 435/254.11; 435/6; 536/23.1; 536/24.31; 536/24.33
(58) Field of Search ............................... 536/23.1, 24.31; 435/320.1, 325, 252.3, 252.33, 254.11, 69.1, 69.5, 69.52, 320

(56) References Cited

U.S. PATENT DOCUMENTS 5,134,076  7/1992  Cunningham et al. .
5,914,253 * 6/1999  Okamura et al. ................. 435/69.52

FOREIGN PATENT DOCUMENTS 05 279 376  10/1993  (JP) .
92/05256    4/1992   (WO) .

OTHER PUBLICATIONS

Okamura, H., et al. *Nature* 378: 88–91, Nov. 1995.*
Bazan, et al, "A newly defined interleukin–1?"; *Nature*, 379:591 (1996).
Laemmli, U.K., "Cleavage of Structural Proteins during the Assembly of the Head of Bacteriophage T4"; *Nature*, 227:680–685 (1970).
Locksley, R.M., "Interleukin 12 in host defense against microbial pathogens"; *PNAS, USA*, 90:5879–5880 (1993).
Nakamura, et al, "Purification of a Factor Which Provides a Costimulatory Signal for Gamma Interferon Production"; *Infect. Immun.*, 61(1):64–70 (1993).
Okamura, et al, "A Novel Costimulatory Factor for Gamma Interferon Induction Found in the Livers of Mice Causes Endotoxic Shock"; *Infect. Immun.*, 63(10):3966–3972 (1995).
O'Sullivan, M. J., "Enzyme Immunoassay" in *Practical Immunoassay*, Butt, W. R., ed., Marcel Dekker, Inc., New York and Basel (1984), pp. 32–69.
Sambrook, et al, *Molecular Cloning: A Laboratory Manual*, Cold Spring Harbor Laboratory Press (1989), pp. v–xxxii.
Toyama and Ando, Eds., *Monoclonal Antibody Experiment Manual*, Japan (1991), pp. 105–152.
Ushio, et al, "Cloning of the cDNA for Human IFN–Gamma–Inducing Factor, Expression in *Escherichia coli*, and Studies on the Biologic Activities of the Protein"; *J. Immunol.*, 156:4274–4279 (1996).

* cited by examiner

Primary Examiner—Lorraine Spector
Assistant Examiner—Dong Jiang
(74) Attorney, Agent, or Firm—Browdy and Neimark

(57) ABSTRACT

A protein which induces the IFN-γ production by immunocompetent cells and has a molecular weight of 19,000±5,000 daltons on SDS-PAGE or gel filtration method and a pI of 4.8±1.0 on chromatofocusing. The protein is isolated from mouse liver and can be purified by a monoclonal antibody specific to it. The monoclonal antibody can be also used for assaying the protein. Fragments of the protein can be used for production of antibodies, and can be produced recombinantly using appropriate medric acids, host cells and vectors. Fragments of nuclear acids may also be used as probes.

11 Claims, 3 Drawing Sheets

DNA MOLECULE ENCODING INTERFERON-GAMMA (IFN-γ) INDUCING FACTOR (IGIF, IL-18) AND DNA FRAGMENT THEREOF

CROSS-REFERENCE TO RELATED APPLICATIONS

The present application is a continuation of application Ser. No. 08/908,005, filed Aug. 11, 1997, issued as U.S. Pat. No. 5,914,253 which is a division of application Ser. No. 08/502,535, filed Jul. 14, 1995, issued as U.S. Pat. No. 5,912,324.

BACKGROUND OF THE INVENTION

1. Field of the Invention

The present invention relates to a protein which induces the interferon-γ (hereinafter abbreviated as "IFN-γ") production by immunocompetent cells, and a monoclonal antibody specific to the protein.

2. Description of the Prior Art

It is said that IFN-γ is a protein which has antiviral-, antioncotic- and immunoregulatory-activities and which is produced by immunocompetent cells stimulated with antigens and/or mitogens. Because of these biological activities, IFN-γ is expected to be used as an antitumor agent since the discovery, and energetically studied on clinical trials as a therapeutic agent for malignant tumors in general including brain tumors. IFN-γ preparations now commercially available are roughly classified into 2 groups, i.e. natural IFN-γs produced by immunocompetent cells and recombinant IFN-γs produced by transformants prepared by introducing DNAs which encode the natural IFN-γs into microorganisms of the species *Escherichia coli*. In such clinical trials, either of these IFN-γs is administered to patients as an "exogenous IFN-γ".

Among these IFN-γs, the natural IFN-γ is usually produced by culturing established immunocompetent cells in nutrient culture media supplemented with IFN-γ inducers to form IFN-γ, and purifying the IFN-γ. It is known that the type of IFN-γ inducers greatly influence on the production yield and the facility of IFN-γ purification, as well as the safeness of the final products. Generally, mitogens such as concanavalin A (Con A), *Lens culinaris*, *Phytolacca americana*, endotoxin and lipopolysaccharide are used. These mitogens, however, have problems of their molecular and quality varying dependently on their origins and purification methods, as well as the difficulty of obtaining a desired amount of preparations with a constant IFN-γ inducibility. In addition, most of these mitogens induce unfavorable side effects when administered to living bodies, and some of them may cause toxicity, so that it is substantially difficult to induce the IFN-γ production by the direct administration to living bodies.

During the study of cytokines produced by mammalian cells, the present inventors have found in mouse liver a novel substance which induces the IFN-γ production. They isolated the substance using two or more conventional purification methods including column chromatography mainly, studied the property and feature and revealing that the reality is a protein having the following physicochemical properties:

(1) Molecular weight 19,000±5,000 daltons on gel filtration sodium dodecylsulfate polyacrylamide gel electrophoresis (SDS-PAGE);

(2) Isoelectric point (pI) 4.8±1.0 on chromatofocusing;

(3) Partial amino acid sequence Possessing partial amino acid sequences corresponding to amino acid residues 26–43 and 79–103 of SEQ ID NO:2

(4) Biological activity Inducing the interferon-γ production by immunocompetent cells.

Such a protein with these physicochemical properties has never been reported, and the data concludes that the protein is novel. The present inventors energetically studied on mouse liver cells and have succeeded to isolate a DNA encoding the protein. The decoding of the protein revealed that the DNA consists of 471 base pairs and encodes the amino acid sequence in SEQ ID NO:3. When the DNA was introduced into microorganisms of the species *Escherichia coli* to express the production of the present protein, the protein was produced in the culture in a satisfactorily high yield. These findings are disclosed in Japanese Patent Application No.184,162/94 applied by the present applicant.

As is described above, the present protein has an activity of inducing the IFN-γ production by immunocompetent cells, and is expected to be used in a variety of uses as an anti-virus agent, antioncotic agent, antiseptic, immunoregulatory agent or a platelet-increasing agent. Generally, in the case of incorporating biologically active proteins into pharmaceuticals, the developments of methods for purifying such proteins highly and effectively and those for assaying samples containing these proteins are inevitable. The material most suitable for the purification and assay is a monoclonal antibody, but such a monoclonal antibody specific to the protein is not established.

SUMMARY OF THE INVENTION

In view of the foregoing, the object of the present invention is to provide a novel protein which induces the IFN-γ production by immunocompetent cells.

It is another object of the present invention to provide a DNA encoding the protein.

It is further object of the present invention to provide a replicable recombinant DNA which contains the DNA and a self-replicable vector.

It is yet another object of the present invention to provide a transformant obtainable by introducing the recombinant DNA into an appropriate host.

It is another object of the present invention to provide a process for preparing the protein by using the recombinant DNA technology.

It is another object of the present invention to provide a novel monoclonal antibody which is specific to the protein having the aforesaid physicochemical properties.

It is another object of the present invention to provide a hybridoma which produces the monoclonal antibody.

It is another object of the present invention to provide a process for preparing the monoclonal antibody.

It is another object of the present invention to provide a purification method with the monoclonal antibody.

It is another object of the present invention to provide a method for detecting the protein with the monoclonal antibody.

The first object of the present invention is attained by a protein having the following physicochemical properties:

(1) Molecular weight 19,000±5,000 daltons on gel filtration and sodium dodecylsulfate polyacrylamide gel electrophoresis (SDS-PAGE);

(2) Isoelectric point (pI) 4.8±1.0 on chromatofocusing;

(3) Partial amino acid sequence Possessing partial amino acid sequences corresponding to amino acid residues 26–43 and 79–103 of SEQ ID NO:2

(4) Biological activity Inducing the IFN-γ production by immunocompetent cells.

The second object of the present invention is attained by a DNA which encodes the protein.

The third object of the present invention is attained by a replicable recombinant DNA which contains the DNA and a self-replicable vector.

The fourth object of the present invention is attained by a transformant obtainable by introducing the replicable recombinant DNA into an appropriate host.

The fifth object of the present invention is attained by a process for preparing the protein comprising culturing the transformant in a nutrient culture medium, and collecting the formed protein from the resultant culture.

The sixth object of the present invention is attained by a monoclonal antibody which is specific to a protein having the following physicochemical properties:

(1) Molecular weight 19,000±5,000 daltons on gel filtration and sodium dodecylsulfate polyacrylamide gel electrophoresis (SDS-PAGE);

(2) Isoelectric point (pI) 4.8±1.0 on chromatofocusing;

(3) Partial amino acid sequence Possessing partial amino acid sequences corresponding to amino acid residues 26–43 and 79–103 of SEQ. ID NO:2

(4) Biological activity Inducing the IFN-γ production by immunocompetent cells.

The seventh object of the present invention is attained by a hybridoma which can produce the monoclonal antibody.

The eighth object of the present invention is attained by a process comprising culturing in vivo or in vitro hybridomas capable of producing the monoclonal antibody, and collecting the monoclonal antibody from the resultant body fluids or cultures.

The ninth object of the present invention is attained by a method for purifying the present protein comprising contacting a monoclonal antibody specific to the protein to a mixture containing the protein and impurities to adsorb the protein on the monoclonal antibody, and desorbing the adsorbed protein from the monoclonal antibody.

The tenth object of the present invention is attained by a method for detecting the present protein comprising contacting the monoclonal antibody with test samples containing the protein to immunologically react them.

BRIEF DESCRIPTION OF THE ACCOMPANYING DRAWINGS

Figure 1:
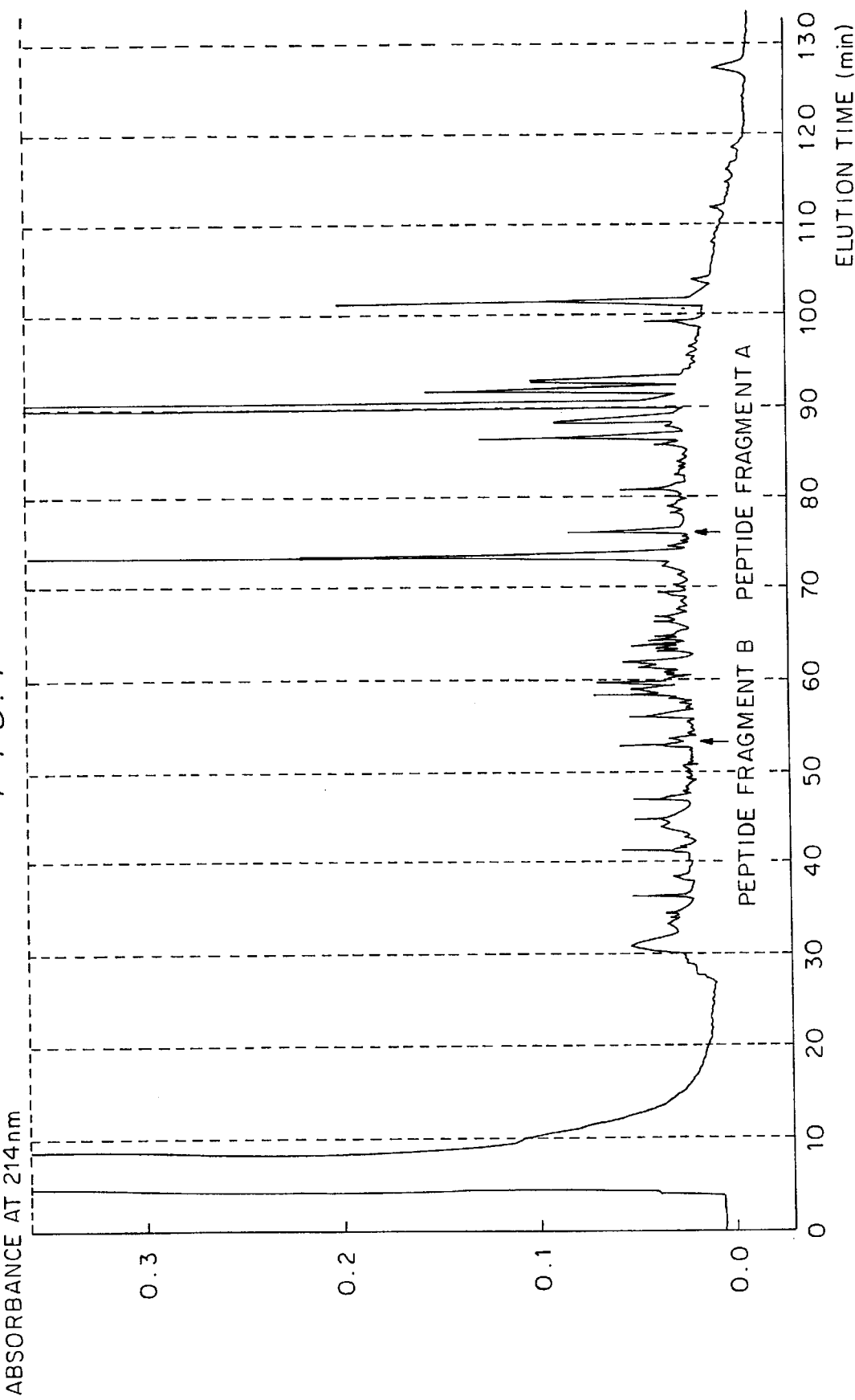
FIG. 1 is an elution pattern of peptide fragments, obtained by trypsinizing the present protein, on high-performance liquid chromatography (HPLC).

In these figures, the symbol "MGTG-1 cDNA" means cDNA which encodes the present protein; "KGFM5 cDNA", cDNA which encodes the present protein; "Ptac", tac promoter; "GST", glutathione S transferase gene; "AmpR", ampicillin resistant gene; "ori", replication initiation site of *Escherichia coli*; and "rrnBT1T2", terminator of ribosome RNA operon.

DETAILED DESCRIPTION OF THE INVENTION

The present invention is based on the finding of a novel protein which induces the IFN-γ production by immunocompetent cells. During studying on cytokines produced from mammalian cells, the present inventors found the existence of a novel substance, which induces the IFN-γ production, in mouse liver. They isolated the substance by combining purification methods comprising column chromatography mainly, studied the property and feature and revealing that the reality is a protein having the following physicochemical properties:

(1) Molecular weight 19,000±5,000 daltons on gel filtration sodium dodecylsulfate polyacrylamide gel electrophoresis (SDS-PAGE);

(2) Isoelectric point (pI) 4.8±1.0 on chromatofocusing;

(3) Partial amino acid sequence Possessing partial amino acid sequences corresponding to amino acid residues 26–43 and 79–103 of SEQ ID NO:2

(4) Biological activity Inducing the interferon-γ production by immunocompetent cells.

The protein according to the present invention has a specific property of inducing the IFN-γ production when acts on immunocompetent cells.

The DNA according to the present invention expresses the production of the present protein by introducing the DNA into an appropriate self-replicable vector to form a recombinant DNA, and introducing the recombinant DNA into a host capable of proliferating without difficulty but inherently incapable of producing the protein.

The replicable recombinant DNA according to the present invention expresses the production of the present protein when introduced into a host capable of proliferating without difficulty but inherently incapable of producing the protein.

The transformant produces the present protein in a desired amount with a relative easiness when cultured by the process according to the present invention.

The present monoclonal antibody specifically reacts with a protein having specific physicochemical properties.

The present hybridoma forms the monoclonal antibody when cultured in vivo and in vitro.

The present process facilitates the production of the monoclonal antibody in a desired amount.

The present purification method yields the present protein with a relatively-high purity from a mixture containing it along with impurities.

In the present detection method, the present protein in test samples only exhibits an immunoreaction, so that the protein is detected quantitatively and qualitatively by monitoring the immunoreaction with a suitable method.

The protein according to the present invention includes proteins in general which have specific physicochemical properties and those derived from natural sources and those prepared by the recombinant DNA technology. The present protein generally has a partially or totally revealed amino acid sequence, for example, the amino acid sequence containing the N-terminal in SEQ ID NO:2 and its homologous amino acid sequences. Variants, which have complementary amino acid sequences to the one in SEQ ID NO:2, can be obtained by replacing one or more amino acids in SEQ ID NO:2 with other amino acids without altering the inherent biological properties of the present protein. Even when used the same DNA and depending on hosts into which the DNA is introduced, as well as on the components of nutrient culture media, the conditions of cultivation temperature and pH for culturing transformants containing the DNA, it may be formed variants, which are defective in or additionally contain one or more amino acids near to the N-terminal in SEQ ID NO:2 while retaining the inherent biological properties of the protein, by the modification with internal enzymes of the hosts after the DNA expression. The present protein includes such variants as long as they induce the IFN-γ production by immunocompetent cells.

The present protein can be prepared by culturing in nutrient culture media transformants with DNAs encoding the protein, and collecting the formed protein from the resultant cultures. The transformants usable in the present invention can be obtained by introducing into appropriate hosts DNAs having the base sequence in SEQ ID NO:1, homologous base sequences to it, and complementary ones to these base sequences. One or more bases in those base sequences can be replaced with other bases by means of the degeneracy of genetic code without alternating the amino acid sequence of the present protein. To express the production of the protein in hosts with such DNAs, one or more bases in base sequences, which encode the present protein or its variants, can be replaced with other bases.

Any DNA can be used in the present invention as long as it has one of those base sequences independently of their origin, i.e. those from natural sources or those prepared by chemical synthesis. The natural sources include, for example, mouse liver cells from which a gene containing the present DNA is obtainable.

The preparation procedure is as follows: Remove mouse liver previously challenged with stimulants such as *Corynebacterium parvum,* BCG (Bacillus Calmette-Guérin, mitogen and lipopolysaccharide, disrupt the liver cells, and isolate the whole DNAs from the resultant suspension. Treat the DNAs with oligo-dT cellulose or oligo-dT latex to obtain poly (A)⁺RNA, and fractionate it using a sucrose density gradient buffer to isolate mRNA. Allow a reverse transcriptase and a polymerase to act on the mRNA as a template to form double-stranded cDNA, introduce the cDNA into an appropriate self-replicable vector, and introduce the resultant recombinant DNA into an appropriate host such as *Escherichia coli.* Culture the resultant transformant in a nutrient culture medium, and collect the proliferated cells containing the DNA encoding the present protein by the colony hybridization method. The DNA according to the present invention is obtainable by treating the transformants with conventional methods. To artificially produce the present DNA, for example, it is prepared by the chemical synthesis based on the base sequence in SEQ ID NO:1, or by introducing a DNA which encodes the amino acid sequence in SEQ ID NO:2 into an appropriate vector to form a recombinant DNA, introducing the recombinant DNA into an appropriate host, culturing the resultant transformant in a nutrient culture medium, isolating the proliferated cells from the culture, and collecting plasmids containing the objective DNA from the cells.

The DNA was generally introduced into hosts in the form of a recombinant DNA. Such a recombinant DNA usually contains the DNA and a self-replicable vector, and it can be readily prepared by the recombinant DNA technology in general if only the DNA is in hand. Examples of such self-replicable vector are plasmid vectors such as pKK223-2, pGEX-2T, pRL-λ, pBTrp2 DNA, pUB110, YEp13, Ti plasmid, Ri plasmid and pBI121. Among these vectors, pKK223-2, pGEX-2T, pRL-λ, pBTrp2 DNA, pUB110 and YEp13 are suitably used when the present DNA is expressed in procaryotes such as yeasts and other microorganisms of the species *Escherichia coli* and *Bacillus subtilis,* while Ti plasmid, Ri plasmid and pBI121 are suitably used for the expression in animal- and plant-cells.

To introduce the present DNA into these vectors, conventional methods used in this field can be arbitrarily used: Genes containing the present DNA and self-replicable vectors are cleaved with restriction enzymes and/or ultrasonic, and the resultant DNA fragments and vector fragments are ligated. To cleave genes and vectors, restriction enzymes which specifically act on nucleotides, more particularly, type II restriction enzymes such as Sau 3AI, Eco RI, Hind III, Bam HI, Sal I, Xba I, Sac I and Pst I, can be used to facilitate the ligation of DNA fragments and vector fragments. To ligate DNA fragments and vector fragments, they are, if necessary, first annealed, then treated with a DNA ligase in vivo or in vitro. The recombinant DNAs thus obtained can be readily introduced into appropriate hosts, and this enables the limitless replication of the DNAs by culturing the transformants.

The recombinant DNAs usable in the present invention can be introduced into appropriate hosts such as yeasts and other microorganisms of the species *Escherichia coli* and *Bacillus subtilis:* When microorganisms of the species *Escherichia coli* are used as a host, they are cultured in the presence of recombinant DNAs and calcium ions, and the competent cell method and the protoplast method are used when microorganisms of the species *Bacillus subtilis* are used as a host. To clone the objective transformants, they are selected by the colony hybridization method or by culturing all the transformants in nutrient culture media, and selecting ones which produce proteins capable of inducing immunocompetent cells to produce IFN-γ.

The transformants thus obtained produce the present protein intracellularly or extracellularly when cultured in nutrient culture media. Examples of such nutrient culture media are those in the form of liquid in general which contain carbon sources, nitrogen sources and minerals, as well as amino acids and/or vitamins as a micronutrient. The carbon sources usable in the present invention include saccharides such as starch, starch hydrolysates, glucose, fructose and sucrose. The nitrogen sources usable in the present invention include organic and inorganic nitrogen-containing compounds such as ammonia and their salts, urea, nitrates, peptone, yeast extract, defatted soy bean, corn steep liquor, and beef extract. The transformants are inoculated into nutrient culture media and incubated at a temperature of 25–65° C. and at a pH of 2–8 for about 1–10 days under aerobic conditions by the agitation-aeration method, etc., to obtain cultures containing the present protein. Although the cultures can be used intact as an IFN-γ inducer, they are, if necessary, subjected to ultrasonication and/or cell lysis enzymes to disrupt cells, followed by filtering or centrifuging the resultant suspensions to remove intact cells and cell debris, and further purifying the resultant supernatants containing the present protein. The purification methods usable in the present invention are, for example, those which are generally used in this field to purify biologically active substances, i.e. concentration, salting out, dialysis, separatory sedimentation, gel filtration chromatography, ion-exchange chromatography, hydrophobic chromatography, affinity chromatography, chromatofocusing, gel electrophoresis, and isoelectric point electrophoresis, and, if necessary, two or more of them can be used in combination. The resultant purified solutions containing the present protein can be concentrated and/or lyophilized into liquids or solids to meet to final uses.

As is described above, the present protein has an activity of inducing IFN-γ production by immunocompetent cells. Because of this, the present protein can be arbitrarily used as therapeutic and/or prophylactic agents, for example, those for virus diseases such as AIDS and condyloma acuminatum; malignant tumors such as renal cancer, granuloma, mycosis fungoides and cerebral tumor; and immune disorders such as articular rheumatism and allergy.

The present protein is allowed to coexist in nutrient culture media to induce the IFN-γ production by immunocompetent cells, or directly administered to mammals for the treatment and/or prevention of IFN-γ susceptive diseases. In the former, leukocytes separated from peripheral blood of mammals, or established immunocompetent cells such as HBL-38 cells, MO cells, Jurkat cells, EL-4 cells and L12-R4 cells are suspended in nutrient culture media containing the present protein to induce the IFN-γ production. If necessary, such nutrient culture media can be supplemented with T-cell stimulants such as mitogen, interleukin 2, and anti-CD 3 antibody, and the cells are cultured at 30–40° C. and at a pH of about 5–8 for about 1–100 hours while the media were replacing with fresh ones. IFN-γ can be obtained from the resultant cultures with one or more conventional methods in general used for purifying biologically active substances, for example, concentration, salting out, dialysis, separatory sedimentation, gel filtration chromatography, ion-exchange chromatography, chromatofocusing, gel electrophoresis, and isoelectric point electrophoresis.

To treat and/or prevent IFN-γ susceptive diseases, the IFN-γ inducing agents according to the present invention are directly administered to mammals: For example, the agents are orally administered to mammals after formulated into appropriate forms, or injected to the mammals intradermally, subcutaneously, muscularly, intravenously and peritoneally. The mammals, which can be administered with the present protein, are not restricted to human, and include other animals such as mouse, rat, hamster, rabbit, dog, cat, caw, horse, coat, sheep, pig and monkey. Since the present protein has a strong IFN-γ inducibility and an extremely-low toxicity, it readily induces the IFN-γ production with only a small amount without causing serious side effects even when administered to in a relatively-large amount. Thus, the present protein induces the desired amount of IFN-γ production smoothly without strictly controlling the administration, so that it can be used as an IFN-γ production inducing agent.

The present protein has a feature of strongly activating the cytotoxicity of killer cells, and, when used in combination with interleukin 2 and/or tumor necrosis factor (TNF), it exerts a strong effect on the therapeutic effect and/or the reduction of side effects in the treatment of adoptive immunotherapy for malignant tumors including solid carcinomas such as lung cancer, renal cancer, and breast cancer.

The monoclonal antibody according to the present invention includes those in general, which are specific to the proteins having the above physicochemical properties independently of their sources, origins and classes. Examples of proteins are those which have the amino acid sequence in SEQ ID NO:2 and its homologous ones. Such homologous amino acid sequences include those wherein one or more amino acids are replaced with other amino acids without substantially alternating the physicochemical properties of the protein, as well as those which one or more amino acids are added to the N- and C-terminals in SEQ ID NO:2, and those which are defective in one or more amino acids in the N- and C-terminals in SEQ ID NO:2.

The present monoclonal antibody can be obtained by using the protein or its antigenic fragments as an antigen. For example, the monoclonal antibody can be obtained by hybridizing antibody-producing cells, collected from mammals which had been immunized with those antigens, with cells that infinitely proliferate, cloning hybridomas capable of producing the present monoclonal antibody, and culturing the clones in nutrient culture media in vitro.

The proteins usable as an antigen in the present invention can be obtained from mouse liver cells as disclosed in Japanese Patent Application No.184,162/94, or obtained by culturing in nutrient culture media transformants into which DNAs encoding the amino acid sequence in SEQ ID NO:2 or its homologous ones are introduced. Generally, they are used in a completely- or partially-purified form. To obtain the antigenic fragments, the resultant completely- or partially-purified proteins are hydrolyzed chemically or enzymatically, or subjected to peptide synthesis using the amino acid sequence in SEQ ID NO:2.

The immunization methods usable in the present invention include conventional ones: For example, those which comprise injecting the antigens with or without adjuvants into mammals intravenously, subcutaneously or intraperitoneally, and feeding the mammals for a prescribed period of time. The mammals usable in the present invention are not specifically restricted to as long as they produce the objective antibody-producing cells independently of their kind, size and sex. Although rodents such as rat, mouse and hamster are generally used, the most suitable mammal is chosen therefrom in view of the adaptivity to the following mammalian cells which infinitely proliferate. Depending on the kind and size of mammals, the total dose of antigens is generally about 5–500 μg/mouse and administered to in 2–5 shots at an interval of about 1–2 weeks. On 3–5 days after the final administration, the spleens of the mammals are extracted and dispersed in nutrient culture media to obtain a spleen cell suspension as an antibody-producing cell.

The resultant cells and mammalian cells capable of infinitely proliferating are hybridized to obtain hybridized cells containing the objective hybridomas. The mammalian cells capable of infinitely proliferating generally include cell lines from mouse bone marrow such as P3-NS1-Ag4-1 cells (ATCC TIB18), P3-X63-Ag8 cells (ATCC TIB9) and SP2/0-Ag14 cells (ATCC CRL1581), and their variants. The methods to fuse cells include conventional methods wherein electric pulses and fusion accelerators such as polyethylene glycol and sendai virus (HVJ) are used. For example, those which comprise suspending antigen-producing cells and mammalian cells capable of infinitely proliferating in a ratio of about 1:1 to 1:10 in cell fusion media containing fusion accelerators, and incubating at about 30–40° C. for about 1–5 min.

The media for cell fusion used in the present invention are those in generally used in this field such as MEM medium, RPMI 1640 medium and Iscove's modified Dulbecco's medium, and it is desirable to exclude serums such as calf serum from the media.

To select the objective hybridoma, the resultant fused cells are transferred to selection media such as HAT medium, incubated at about 30–40° C. for about 3 days to 3 weeks to die cells other than the objective hybridomas. The hybridomas are cultured in usual manner, and the antibody secreted in the culture is tested for reactivity with the present protein. Conventional assays for detecting antigens such as enzyme immunoassay, radioimmunoassay and bioassay are used in this experiment. For example, these assays are described in detail in "*Tan-kuron Kotai Jikken Manual* (Monoclonal Antibody Experimental Manual)", edited by Sakuji TOYAMA and Tamie ANDO, pp.105–152 (1991). Hybridomas capable of producing antibodies specific to the present protein are speedily cloned by the limiting dilution to obtain the present hybridoma.

The monoclonal antibody according to the present invention can be obtained by culturing the present hydridoma in vivo or in vitro. The culture methods usable in the present invention include conventional ones used for culturing mammalian cells. For example, in the case of in vitro culture, the monoclonal antibody is collected from the resultant culture, while in the case of in vivo culture wherein the hybridoma is transplanted in warm-blooded animals and cultured in the bodies, the monoclonal antibody is collected from the animals's ascites or blood. The later described hybridoma M-1 is characteristic of a relatively-high productivity of the monoclonal antibody and a readily proliferation in vivo and in vitro. The methods for collecting the monoclonal antibody from the resultant cultures, ascites and blood include conventional methods generally used in this field to purify antibodies in general. For example, salting out, dialysis, filtration, concentration, centrifugation, separatory sedimentation, gel filtration chromatography, ion-exchange chromatography, affinity chromatography, high-performance liquid chromatography (HPLC), gel electrophoresis and isoelectric point electrophoresis, can be used alone or in combination. The purified monoclonal antibody is concentrated and/or dried into a liquid or solid form to meet to final use.

The monoclonal antibody according to the present invention is extremely useful in the purification of the present protein on immunoaffinity chromatography. Such a purification method comprises a step of contacting the present monoclonal antibody with a mixture containing the present protein and impurities, and a step of desorbing the adsorbed protein from the monoclonal antibody. These steps are usually carried out in an aqueous medium. The present monoclonal antibody is generally used under the conditions of coupling to aqueous carriers in a gel form which are packed in cylindrical columns, followed by feeding to the columns with mouse liver cell extracts, cultures of transformants, or their partially purified products to substantially adsorb the protein on the monoclonal antibody. The adsorbed protein is readily desorbed by changing the pH around the monoclonal antibody, for example, in the case of using a monoclonal antibody belonging to IgG class, the present protein is eluted therefrom at an acid pH, usually, a pH of 2–3, while in the case of using a monoclonal antibody belonging to IgM class, it is eluted at an alkaline pH, usually, a pH of 10–11.

The present purification method can purify the present protein with the minimum labor cost and time. As is described above, the present protein has an activity of inducing the IFN-γ production by immunocompetent cells, so that the resultant purified protein can be used as an inducer for the IFN-γ production by cell culturing methods, and can be arbitrarily used as a therapeutic and/or prophylactic agent for viral diseases such as AIDS and condyloma, malignant tumors such as renal cancer, granuloma, mycosis fungoides and cerebral tumor. When the protein according to the present invention has an activity of increasing the cytotoxicity of killer cells, it can be used in combination with interleukin 2 and/or tumor necrosis factor to exert a remarkable efficacy on the therapeutic effect in the treatment of malignant tumors including solid carcinomas such as lung cancer, renal cancer and breast cancer, and it also decreases the side effects.

The monoclonal antibody according to the present invention is widely useful in the field where the detection of the present protein is required. When the present monoclonal antibody is used in combination with labeled immunoassays such as radioimmunoassay, enzyme immunoassay and fluorescent immunoassay, the present protein in test samples is quickly and accurately quantified or qualified. In such analyses, the present monoclonal antibody is labeled with radioactive substances, enzymes and/or fluorescent substances prior to use. Since the present monoclonal antibody specifically binds to the present protein to cause an immunoreaction, a trace amount of the present protein in test samples can be detected by measuring the level of the immunoreaction based on these labeled substances as a marker. As compared with bioassays, labeled immunoassays have features that it can assay many samples at the same time in a relatively short time, low labor-cost, and high accuracy. Therefore, the present detection method is extremely useful for controlling the steps in the preparation of the present protein and in the quality control of the final products. Although the present invention does not describe in detail the method for labeling monoclonal antibodies and the labeled assays because the present invention in itself does not relate to them, examples of such are described by P. Tijssen in *"Practice and Theory of Enzyme Immunoassays"*, pp.196–347 (1989).

The following experiments describe the present protein:

Experiment 1

Preparation of purified protein

To 600 8-week-old female CD-1 mice was intraperitonealy injected one mg/mouse of dead *Corynebacterium parvum* (ATCC 11827) which had been obtained by preheating at 60° C. for one hour, and the mice were fed in usual manner for 7 days and intravenously injected with one µg/mouse of a purified lipopolysaccharide derived from *Escherichia coli*. On 1–2 hours after the intravenous injection, the mice were sacrificed by dislocating their cervical vertebrae to collect their blood from hearts, followed by removing their livers, disrupting them by a homogenizer in 8-fold volumes of 50 mM phosphate buffer (pH 7.3), and extracting the resultant. The resultant extract was centrifuged at about 8,000 rpm for 20 min, and an about 9 L of the resultant supernatant was admixed with a saturated ammonium sulfate in 50 mM phosphate buffer (pH 7.3) to give a saturation degree of 45 w/v %. The resultant solution was allowed to stand at 4° C. for 18 hours and centrifuged at about 8,000 rpm for 30 min to obtain a 19 L supernatant containing the present protein.

The supernatant was fed to a column packed with about 4.6 L of "PHENYL SEPHAROSE", a product of Pharmacia LKB, Uppsala Sweden, which had been equilibrated with 50 mM phosphate buffer (pH 7.3) containing one M ammonium sulfate, and the column was washed with a fresh preparation of the same buffer, and fed at an SV (space velocity) 0.57 with a linear gradient of ammonium sulfate ranging from 1 M to 0.2 M in 50 mM phosphate buffer (pH 7.3). Fractions containing the present protein eluted at 0.8 M ammonium sulfate were collected and pooled into an about 4.8 L solution which was then concentrated with a membrane filter, dialyzed against 20 mM phosphate buffer (pH 6.5) at 4° C. for 18 hours, and fed to a column packed with about 250 ml of "DEAE-SEPHAROSE", a product of Pharmacia LKB, Uppsala, Sweden. The column was washed with a fresh preparation of the same buffer and fed at an SV 1.2 with a linear gradient of sodium chloride ranging from 0 M to 0.2 M in 20 mM phosphate buffer (pH 6.5) to elute the present protein at a concentration of about 0.13 M sodium chloride.

Fractions containing the present protein were collected, pooled (about 260 ml), concentrated and dialyzed against 25 mM Bis-Tris buffer (pH 7.1) at 4° C. for 18 hours. The dialyzed solution was applied to a column packed with about 24 ml of "MONO-P", a product of Pharmacia LKB, Uppsala, Sweden, and eluted with 10 v/v % polybuffer 74 (pH 4.0) while decreasing the pH from 7 to 4 to obtain an about 23 ml eluate containing the present protein. The eluate was concentrated, fed to a column packed with "SUPER- DEX 75", a product of Pharmacia LKB, Uppsala, Sweden, which had been equilibrated with a solution containing 7 mM disodium hydrogen phosphate, 3 mM sodium dihydrogen phosphate, and 139 mM sodium chloride, and eluted with a fresh preparation of the same solution on gel filtration chromatography to obtain fractions containing the present protein, eluted at fractions corresponding to about 19,000 daltons. The fractions were pooled and concentrated for use in Experiment 2. The yield of the present protein was about 0.6 µg/mouse.

Experiment 2

Physicochemical property of protein

Experiment 2-1

Molecular weight

In accordance with the method reported by U. K. Laemmli in *Nature,* Vol.227, pp.680–685 (1970), the purified protein prepared by the method in Experiment 1 was electrophoresed in a sodium dodecylsulfate (SDS) polyacrylamide gel free of reducing agent to mainly show a single protein band with an IFN-γ inducing activity at a position corresponding to about 19,000±5,000 daltons. The marker proteins used in this experiment were calf serum albumin (MW=67,000 daltons), ovalbumin (MW=45,000 daltons), soy bean trypsin inhibitor (MW=20,100 daltons), and α-lactalbumin (MW=14,400 daltons).

Experiment 2-2

Isoelectric point

The purified protein in Experiment 1 was chromatofocused to give an isoelectric point of about 4.8±1.0.

Experiment 2-3

Partial amino acid sequence

A portion of an aqueous solution containing the purified protein in Experiment 1 was concentrated up to a volume of about 50 µl which was then admixed with 25 µl of a solution containing 3 w/v % SDS, 60 v/v % glycerol, and 60 mg/ml dithiothreitol. The resultant mixture was incubated at 50° C. for 30 min, positioned on 15 w/v % polyacrylamide gel, and electrophoresed in usual manner. The resultant gel was stained by soaking it in a mixture solution of 10 v/v % aqueous acetic acid solution and 50 v/v % aqueous methanol solution containing 0.1 w/v % coomassie brilliant blue R 250, destained by repeatedly washing the gel with a mixture solution of 12 v/v % aqueous methanol solution and 7 v/v % aqueous acetic acid solution, and washed by soaking the gel in distilled water for 18 hours. A portion, which was stained with the coomassie brilliant blue and contained the present protein, was cut out of the gel, and lyophilized.

The lyophilized gel was soaked in 0.6 ml aqueous solution consisting of 100 mM sodium hydrogen carbonate containing 2 µg/ml "TPCK TRYPSIN", 0.5 mM calcium chloride, and 0.02 v/v % aqueous Tween 20 solution, followed by the incubation at 37° C. for 18 hours to trypsinize the protein. The resultant was centrifuged to obtain a supernatant, while the resultant precipitate was soaked in one ml of one v/v % aqueous trifluoroacetate containing 0.001 v/v % Tween 20, shook for 4 hours at ambient temperature, and centrifuged to obtain a supernatant. The newly formed precipitate was successively treated similarly as above with 70 v/v % aqueous trifluoroacetate containing 0.001 v/v Tween 20 and with 50 v/v % aqueous acetonitrile to obtain a supernatant. The resultant supernatant and the above supernatant already obtained in the above were pooled and concentrated up to 250 µl, and the concentrate was centrifugally filtered.

The resultant aqueous solution containing peptide fragments was fed to "HPLC ODS-120T", a column for HPLC commercialized by Tosoh Corporation, Tokyo, Japan, which had been previously equilibrated with 0.1 v/v aqueous trifluoroacetate, and the column was washed with 0.1 v/v % aqueous trifluoro acetate, and fed with 0.1 v/v % trifluoro acetate at a flow rate of 0.5 ml/min while the concentration of aqueous acetonitrile was increasing from 0 v/v % to 70 v/v % and the concentration of peptide in the eluate was monitoring by a spectrophotometer at wave lengths of 214 nm and 280 nm. Fractions eluted about 75 min and about 55 min after the initiation of the elution were respectively collected (hereinafter named "peptide fragment A" and "peptide fragment B"). The elution pattern was in FIG. 1.

The peptide fragments A and B were analyzed on "MODEL 473 A", a protein sequencer commercialized by Perkin-Elmer Corp., Instrument Div., Norwalk, USA, and revealing that they have the amino acid sequences corresponding to amino acid residues 26–43 and 79–103 of SEQ ID NO:2.

Experiment 2-4

Biological activity

Experiment 2-4(a)

Induction of the IFN-γ production by immunocompetent cell

BDF1 Female mouse spleen, 8-week-old, was extracted and dispersed in serum-free RPMI 1640 medium (pH 7.4), and the cells were washed with a fresh preparation of the same medium, and soaked in Gei buffer (pH 8.0) to hemolyze. The resultant spleen cells were suspended in RPMI 1640 medium (pH 7.4) supplemented with 10 v/v % calf serum to give a cell density of $1\times10^7$ cells/ml, fed to a cell-separatory nylon wool column commercialized by Wako Pure Chemical Industries, Ltd., Tokyo, Japan, and incubated in an incubator at 37° C. for an hour under 5 v/v % $CO_2$ conditions. Thereafter, T-cells were collected from the column by feeding to the column with RPMI 1640 medium (pH 7.4) supplemented with 10 v/v % calf serum, and washed with a fresh preparation of the same buffer. The resultant cells were used in the following experiment for IFN-γ induction.

0.15 ml aliquots of a mouse T-cell suspension in RPMI 1640 medium (pH 7.4) with a cell density of $1\times10^7$ cells/ml were injected into 96-well microplates, and to each well was added a present purified protein, which had been diluted with 0.05 ml RPMI 1640 medium (pH 7.4) supplemented with 10 v/v % calf serum albumin. The cells in the microplates were incubated in the presence or in the absence of 0.5 µg/ml concanavalin A in an incubator at 37° C. for 24 hours under 5 v/v % $CO_2$ conditions. From each well 0.1 ml of the culture supernatant was collected and assayed for IFN-γ production level by conventional enzyme immunoassay (EIA). As a control, a sample free of the present purified protein was provided and treated similarly as above. The standard mouse IFN-γ preparation Gg02-901-533, obtained from The National Institutes of Health, USA, was used as an IFN-γ standard in this experiment, and the activity was expressed in terms of international units (IU).

As a result, no significant IFN-γ production was found with the control sample but found with the test sample: The present protein induced about 2–2,000 IU IFN-γ and about 2–200 IU IFN-γ from $1\times10^6$ mouse T-cells when the T-cells were respectively incubated with and without 0.02–10 µg/ml of concanavalin A. The results confirm that the present protein has an activity of inducing the IFN-γ induction by immunocompetent cells.

Throughout the present specification, one unit activity of the present protein is defined as an amount of which induces 160 IU IFN-γ production when assayed in the presence of concanavalin A (0.5 µg/ml).

Experiment 2-4(b)

Augmentation of cytotoxicity of killer cell

Similarly as in Experiment 2-4(a) mouse spleen cells were suspended in RPMI 1640 medium (pH 7.2) containing 100 μg/ml kanamycin, $5\times10^5$ M 2-mercaptoethanol, and 10 v/v % calf serum to give a cell density of $1\times10^7$ cells/ml. The cell suspension was mixed with 0, 1, 5 or 10 units/ml of a recombinant human interleukin 2, placed in a 25-ml culture flask, admixed with 0, 0.8, 4, 20 or 100 units/ml of the purified protein, and incubated in an incubator at 37° C. for 72 hours under 5 v/v % $CO_2$ conditions. Thereafter, the resultant cells were washed with a fresh preparation of the same RPMI 1640 medium (pH 7.2), and suspended together with YAC-1 cells (ATCC TIB160), which were previously labeled with radioactive sodium chromate, to give a cell ratio of 20/1 or 40/1 (effective cells/target cells) in a fresh preparation of the same RPMI 1640 medium (pH 7.2). The cell suspension was poured in 96-well microplates and incubated in an incubator at 37° C. for 4 hours under 5 v/v % $CO_2$ conditions, followed by determining the radioactivity of $^{51}Cr$ in the resultant supernatant by a γ-ray counter. The results were in Table 1.

The results in Table 1 show that the present protein has an activity of inducing the cytotoxicity of killer cells, and the activity is augmented by interleukin 2.

TABLE 1

| Factor | | Cytotoxicity (%) Ratio | |
| --- | --- | --- | --- |
| The present protein | Interleukin 2 | (Effective cells/Target cells) | |
| (unit/ml) | (unit/ml) | 40/1 | 20/1 |
| 100 | 0 | 48.6 | 46.0 |
| 20 | 0 | 35.5 | 27.5 |
| 4 | 0 | 33.0 | 17.7 |
| 0.8 | 0 | 22.9 | 14.5 |
| 0 | 0 | 0.1 | 0.0 |
| 100 | 1 | 55.8 | 55.2 |
| 20 | 1 | 54.2 | 46.4 |
| 4 | 1 | 40.5 | 26.4 |
| 0.8 | 1 | 22.1 | 10.3 |
| 0 | 1 | 0.4 | 0.0 |
| 100 | 5 | 63.6 | 59.1 |
| 20 | 5 | 62.2 | 49.1 |
| 4 | 5 | 56.2 | 44.6 |
| 0.8 | 5 | 38.4 | 23.4 |
| 0 | 5 | 1.0 | 0.2 |
| 100 | 10 | 67.8 | 56.5 |
| 20 | 10 | 67.7 | 59.9 |
| 4 | 10 | 62.8 | 54.1 |
| 0.8 | 10 | 46.2 | 31.7 |
| 0 | 10 | 1.0 | 0.5 |

No protein having the above identified physicochemical properties has been known, and this confirms that it is a novel protein. The present inventors isolated mRNA from mouse liver cells, collected a DNA fragment which partially encodes the present protein by the reverse transcription-polymerase chain reaction (RT-PCR) in the presence of a primer which was chemically synthesized by using the mRNA as a template based on the partial amino acid sequence revealed in Experiment 2-3, and energetically studied a cDNA library, prepared from the mRNA by using the DNA fragment as a probe, to obtain a DNA fragment in SEQ ID NO:1 which contains the 5'-terminus and consists of 471 base pairs. The decoding of the base sequence revealed that the present protein contains an amino acid sequence in SEQ ID NO:2 which consists of 157 amino acids and contains the N-terminal. In SEQ ID NO:2 the symbol "Xaa" as an amino acid means "Met (methionine)" or "Thr (threonine)".

The sequential techniques used to reveal the amino acid sequence and base sequence in SEQ ID NOs:2 and 1 are summarized in the below:

(1) The present protein is isolated from mouse liver cells and highly purified by combining conventional purification methods comprising chromatography as a main technique;

(2) The resultant purified protein was digested with trypsin, and 2 polypeptide fragments were isolated from the resultant mixture and determined for amino acid sequence;

(3) From mouse liver cells, mRNA was collected, and a DNA fragment which partially encodes the present protein was prepared by the reverse transcription-polymerase chain reaction (RT-PCR) in the presence of a primer which was chemically synthesized by using the mRNA as a template based on the partial amino acid sequences revealed in the above. The DNA fragments were screened by using an oligonucleotide as a probe which had been chemically synthesized based on these partial amino acid sequences, followed by collecting a DNA fragment which partially encodes the present protein;

(4) A cDNA library was prepared with the mRNA as a template and hybridized with the DNA fragment as a probe, followed by collecting a transformant which strongly hybridized with the DNA fragment; and (5) A cDNA was isolated from the transformant, and the base sequence was determined and decoded. The comparison of the decoded amino acid sequence and the partial amino acid sequence revealed that the base sequence encodes the present protein.

The following Experiment 3 is to explain the above techniques (3) to (5), and the techniques in themselves used therein are commonly known in the art, for example, those disclosed by J. Sumbrook et al. in "*Molecular Cloning, A Laboratory Manual*", 2nd edition (1989), published by Cold Spring Harbor Laboratory Press, New York, USA, and by Masami MURAMATSU in "*Rabo-Manual for Genetic Technology*" (1988), published by Maruzen Co., Ltd., Tokyo, Japan.

Experiment 3

Base sequence of DNA and amino acid sequence of protein

Experiment 3-1

Preparation of whole RNA

Three g of wet mouse liver cells, similarly prepared by the method in Experiment 1, was weighed, soaked in 20 ml of a mixture solution containing 6 M guanidine isothiocyanate, 10 mM sodium citrate, and 0.5 w/v SDS, and disrupted with a homogenizer. 35-ml centrifugation tubes were injected with 25 ml of 0.1 M EDTA (pH 7.5) containing 5.7 M cesium chloride, and 10 ml of the homogenized cells were overlaid on the upper part of the solutions in the tubes, followed by centrifuging the tubes at 25,000 rpm for 20 hours to collect RNA fractions. The fractions were pooled, distributed into 15-ml centrifugation tubes, and mixed with equal volumes of a mixture solution of chloroform and isobutanol (=4:1 by volume). The tubes were vibrated for 5 min and centrifuged at 4° C. and at 10,000 rpm for 10 min, and the formed water layers were collected, pooled, mixed with 2.5-fold volumes of ethanol, and allowed to stand at −20° C. for 2 hours to precipitate the whole RNAs. The precipitate was collected, pooled, washed with 75 v/v % aqueous ethanol solution, and dissolved in 0.5 ml of sterilized distilled-water for use in the following experiment. The yield of the RNAs was about 4 mg, on a dry solid basis (d.s.b.).

Experiment 3-2

Preparation of DNA fragments encoding partially the present protein

One μg of the whole RNAs in Experiment 3-1 was mixed with 4 μl of 25 mM magnesium chloride, 2 μl of a solution of 10×PCR buffer consisting of 100 mM Tris-HCl buffer (pH 8.3) and 500 mM potassium chloride, 8 μl of one mM dNTP mix, one μl of a solution containing one unit/μl RNase inhibitor, one μl of a solution containing 2.5 units/μl reverse transcriptase, and one μl of 2.5 μM random hexamer, and further mixed with sterilized distilled-water to give a total volume of 20 μl. The mixture solution was placed in 0.5 ml reaction tubes, and, in usual manner, successively incubated at 25° C. for 10 min, at 42° C. for 30 min, at 99° C. for 5 min, and at 5° C. for 5 min to effect the reverse transcriptase reaction, followed by recovering an aqueous solution containing the first strand cDNA.

To 20 μl of the aqueous solution were added 4 μl of 25 mM magnesium chloride, 8 μl of 10×PCR buffer, 0.5 μl of a solution containing 2.5 units/μl of AmpliTaq DNA polymerase commercialized by Perkin-Elmer Corp., Instrument Div., Norwalk, USA, and one pmole of primer 1 or 2 as a sense primer or an anti-sense primer. The mixture solution was volumed up to 100 μl with sterilized distilled-water, and, in usual manner, successively incubated at 94° C. for one min, at 45° C. for 2 min, and at 72° C. for 3 min in a cyclic manner for 40 cycles to amplify a DNA fragment, which partially encodes the present protein, by using the first strand cDNA as a template. The primers 1 and 2 are oligonucleotides, which were chemically synthesized based on the amino acid sequences of Pro-Glu-Asn-Ile-Asp-Asp-Ile (residues 29–35 of SEQ ID NO:2) and Phe-Glu-Asp-Met-Thr-Asp-Ile (residues 29–35 of SEQ ID NOL2) in SEQ ID NOs:1 and 2, and they have base sequences of 5'-ATRTCRTCDATRTTYTCNGG-3' and 5'-TTYGARGAYATGACNGAYAT-3'(SEQ ID NO:4), respectively.

A portion of the resultant PCR product was fractionated on electrophoresis in 2 w/v % agarose gel, transferred onto a nylon film, fixed with 0.4 N sodium hydroxide, washed with 2×SSC, air-dried, soaked in a prehybridization solution containing 5×SSPE, 5×Denhard's solution, 0.5 w/v % SDS and 100 μg/ml of denatured salmon sperm DNA, and incubated at 65° C. for 3 hours. An oligonucleotide as a probe 1 having a base sequence of 5'-TTYGARGARATGGAYCC-3'(SEQ ID NO:5) was synthesized based on the amino acid sequence of Phe-Glu-Glu-Met-Asp-Pro in corresponding to amino acid residues 82–87 of SEQ ID NO:2, and labeled with [γ-$^{32}$P]ATP and T4 polynucleotide kinase. The nylon film was soaked in a solution containing one pmole of the probe 1, 5×SSPE, 5×Denhardt's solution, 0.5 w/v % SDS, and 100 μg/ml of a denatured salmon sperm DNA, and incubated at 45° C. for 24 hours to effect hybridization. The resultant nylon film was washed with 6×SSC and autoradiographed in usual manner and revealing that the PCR product contained the objective DNA fragment.

The remaining PCR product was mixed with "pT7 BLUE T", a plasmid vector commercialized by Takara Shuzo Co., Ltd., Tokyo, Japan, an adequate amount of T4 ligase, and further mixed with 100 mM ATP up to give a concentration of one mM, followed by the incubation at 16° C. for 18 hours to insert the DNA fragment into the plasmid vector. The recombinant DNA thus obtained was introduced into *Escherichia coli* NoVa Blue strain, a microorganism of the species *Escherichia coli* commercialized by Pharmacia LKB, Uppsala, Sweden, to obtain a transformant which was then inoculated into a medium plate containing 10 g/l bactotryptone, 2.5 g/l sodium chloride, 15 g/l bacto-agar, 100 mg/l ampicillin, 40 mg/l X-Gal and 23.8 mg/l isopropyl-β-D-thiogalacto-pyranoside (hereinafter abbreviated as "IPTG"), and incubated at 37° C. for 24 hours to form colonies. A nylon film was in usual manner positioned on a medium plate and allowed to stand for about 30 seconds to attach the colonies thereunto. The nylon film was then detached from the medium plate and soaked for 7 min in a solution containing 0.5 N sodium hydroxide and 1.5 M sodium chloride to effect cell lysis. Thereafter, the nylon film was soaked for 3 min in 1.5 M sodium chloride in 0.5 M Tris-HCl buffer (pH 7.2), washed with 2×SSC, soaked in 0.4 N sodium hydroxide for 20 min to fix the DNA, washed with 5×SSC, air-dried, soaked in a prehybridization solution containing 5×SSPE, 5×Denhardt's solution, 0.5 w/v % SDS, and 100 μg/ml denatured salmon sperm DNA, and incubated at 65° C. for 3 hours. The colonies on the nylon film were in usual manner hybridized with the probe 1, washed with 6×SSC, and autoradiographed similarly as above, followed by selecting from the medium plate transformants which strongly hybridized with the probe 1.

The transformants were inoculated in L-broth (pH 7.2) containing 100 μg/ml ampicillin and incubated at 37° C. for 18 hours, followed by collecting cells from the culture and collecting recombinant DNA by conventional SDS-alkali method. The analysis of the dideoxy method revealed that the recombinant DNA contained a DNA fragment consisting of base sequences which correspond to those at positions from 85 to 281 in SEQ ID NO:1.

Experiment 3-3

Preparation of mRNA 0.05 ml of an aqueous solution containing the whole RNAs in Experiment 3-1 was placed in a test tube, admixed with 0.5 ml of 10 mM Tris-HCl buffer (pH 7.5) containing one mM EDTA and 0.1 w/v % SDS, and volumed up to one ml with sterilized distilled-water. To the mixture was added one ml "OLIGOTEX-dT30 SUPER", an oligo-d(T)$_{30}$ latex commercialized by Nippon Roche K.K., Tokyo, Japan, followed by the incubation at 65° C. for 5 min to denature the RNAs and the cooling for 3 min in an ice-chilled bath. The resultant mixture was admixed with 0.2 ml of 5 M sodium chloride, incubated at 37° C. for 10 min, and centrifuged at 10,000 rpm at 25° C. for 10 min. The precipitate in the form of a pellet was suspended in 0.5 ml sterilized distilled-water, and incubated at 65° C. for 5 min to extract mRNA from the oligo-d(T)$_{30}$ latex. The yield of the mRNA was about 5 μg.

Experiment 3-4

Preparation of cDNA library cDNA Library was prepared from the mRNA in Experiment 3-3 by using "cDNA SYNTHESIZING SYSTEM PLUS", a cDNA cloning kit commercialized by Amersham Corp., Div., Amersham International, Arlington Heights, USA. The procedures were as follows: To 1.5-ml reaction tube were successively added 4 μl of a solution for synthesizing the first strand cDNA, one μl sodium pyrophosphate solution, one μl of a solution of human placenta ribonuclease inhibitor, 2 μl deoxynucleotide triphosphate mix, and one μl oligo-dT primer. The resultant mixture was mixed with 2 μl of mRNA in Experiment 3-3, volumed up to 19 μl with sterilized distilled-water, mixed with one μl of a solution containing 20 units of reverse transcriptase, and incubated at 42° C. for 40 min to obtain a reaction mixture containing the first strand cDNA.

The mixture thus obtained was mixed with 37.5 μl of a solution for synthesizing the second strand cDNA, 0.8 units of ribonuclease H derived from *Escherichia coli*, and 23 units of DNA polymerase, and volumed up to 100 μl with sterilized distilled-water. The resultant mixture was successively incubated at 12° C. for 60 min and at 22° C. for 60 min, mixed with 2 units of T4 DNA polymerase, and incubated at 37° C. for 10 min to obtain a reaction mixture containing the second strand cDNA. To the reaction mixture was added 4 μl of 0.25 M EDTA (pH 8.0) to suspend the reaction, and the resultant was in usual manner extracted with phenol and chloroform and treated with ethanol to precipitate the objective cDNA, followed by recovering the precipitate.

To the cDNA thus obtained were added 2 μl L/K buffer, 250 pmole Eco RI adaptor, and 2.5 units of T4 DNA ligase in this order, and the resultant solution was volumed up to 20 μl with sterilized distilled-water, and incubated at 15° C. for 16 hours to ligate the Eco RI adaptor to the both ends of the cDNA. The reaction mixture was mixed with 2 μl of 0.25 M EDTA to inactivate the remaining enzyme, and subjected to molecular sieve chromatography to remove intact Eco RI adaptor. To the resultant were added 40 μl L/K buffer and 80 units of T4 polynucleotide kinase, and the mixture was volumed up to 400 μl with sterilized distilled-water, followed by the incubation at 37° C. for 30 min to methylate the Eco RI cleavage sites. The resultant mixture was extracted with phenol and chloroform and treated with ethanol to precipitate the objective DNA, followed by recovering the DNA. To the DNA were added 1.5 μl of L/K buffer containing an adequate amount of λgt 10 arms, and 2.5 units of T4 DNA ligase, and the resultant solution was volumed up to 15 μl with sterilized distilled-water, incubated at 15° C. for 16 hours to effect ligation, and subjected to conventional in vitro packaging method to obtain a phage containing a recombinant EDNA.

Experiment 3-5

Cloning of recombinant DNA

A seed culture of *Escherichia coli* NM514 strain was in usual manner infected with the phage in Experiment 3-4, and the infected cells were inoculated in an agar plate (pH 7.0) containing 10 g/l bactotrypton, 5 g/l bacto-yeast extract, 10 g/l sodium chloride and 15 g/l bacto-agar, and incubated at 37° C. for 6 hours to form plaques. The agar plate was covered with a nylon film and allowed to stand for about 30 seconds to attach the plaques thereunto. The nylon film was detached from the plate, and successively soaked in an aqueous solution containing 0.5 M sodium hydroxide and 1.5 M sodium chloride for 2 min and in 0.5 M Tris-HCl buffer (pH 7.0) containing 1.5 M sodium chloride for 5 min. The nylon film was washed with 5×SSC, air-dried, soaked in a solution containing 5×SSPE, 5×Denhardt's solution, 0.5 w/v % SDS, and 100 μg/ml denatured salmon sperm DNA, and incubated at 65° C. for 3 hours. Thereafter, the resultant nylon film was incubated in a solution containing an adequate amount of DNA fragment as a probe 2 obtained in Experiment 3-2 and labeled with $^{32}$P by "READY PRIME DNA LABELLING SYSTEM", a DNA labeling kit commercialized by Amersham Corp., Div., Amersham International, Arlington Heights, USA, 5×SSPE, 5×Denhardt's solution, 0.5 w/v % SDS, and 100 μg/ml of denatured salmon sperm DNA, and the mixture was incubated at 60° C. for 20 hours to effect hybridization. The resultant was subjected to autoradiography similarly as above to select phage DNA clones which strongly hybridized with the probe 2.

With conventional techniques, the clones were amplified in *Escherichia coli*, followed by the extraction of a recombinant DNA from the cells. The recombinant DNA was cleaved with Eco RI, a restriction enzyme. Plasmid vector pUC19 (ATCC 37254) was cleaved with the same restriction enzyme, and the resultant cleaved DNA fragments and plasmid fragments were ligated with DNA ligase to obtain a recombinant DNA which was then introduced into *Escherichia coli* JM109 (ATCC 53323) by conventional competent cell method to obtain a transformant.

Experiment 3-6

Determination of base sequence and amino acid sequence

The transformant in Experiment 3-5 was inoculated into L-broth (pH 7.2) and cultured at 37° C. for 18 hours under shaking conditions. The resultant proliferated cells were collected and treated with conventional SDS-alkali method to obtain a recombinant DNA containing the DNA according to the present invention. The analysis on an automatic sequencer using a fluorophotometer revealed that the recombinant DNA contains the base sequence from the 5'-terminus in SEQ ID NO:1. The decoding of the base sequence indicated that it encodes the amino acid sequence containing the N-terminal in SEQ ID NO:1. The amino acid sequence contains the partial amino acid sequences corresponding to those at positions from 79 to 103 and from 26 to 43 in SEQ ID NO:2, and this means that the present protein contains the amino acid sequence containing the N-terminal in SEQ ID NO:2, and that it is encoded by a DNA containing the base sequence from the 5'-terminus in SEQ ID NO:2.

As is described above, the present inventors have found the present protein, which induces IFN-γ production by immunocompetent cells, through their long term research. Unlike conventional proteins, the present protein has specific physicochemical properties. The present invention is to provide the protein by applying the recombinant DNA technology.

The preparation of the present protein using the transformants will be explained in detail with reference to the following Examples:

EXAMPLE 1

Replicable recombinant DNA and transformant

The first strand cDNA was prepared from the whole RNAs in Experiment 3-1 by using "GeneAmp RNA PCR Kit", a PCR kit commercialized by Takara Shuzo Co., Ltd., Tokyo, Japan. The procedures were as follows: To a 0.5-ml reaction tube were added 4 μl of 25 mM magnesium chloride, 2 μl of 10×PCR buffer, 8 μl of one mM dNTP mix, one μl of one unit/μl RNase inhibitor, one μl of 2.5 units/μl of reverse transcriptase, one μl of 2.5 μM random hexamer, and one μl of the whole RNAs in Experiment 3-1, and the mixture was volumed up to 20 μl with sterilized distilled-water. The resultant mixture was successively incubated at 25° C. for 10 min, at 42° C. for 30 min, at 99° C. for 5 min, and at 5° C. for 5 min to obtain a reaction mixture containing the first strand cDNA.

Twenty μl of the reaction mixture was mixed with 4 μl of 25 mM magnesium chloride, 8 μl of 10×PCR buffer, 0.5 μl of 2.5 units/μl of AmpliTaq DNA polymerase, and adequate amounts of sense primer and anti-sense primer as shown by the base sequences of 5'-CGAGGGATCGAACTTTGGCCGACTTC-3(SEQ ID NO:6) and 5'-CGAGGAATTCCTAACTTTGATGTAAG-3' (SEQ ID NO:7) which were chemically synthesized based on the amino acid sequences near to the N- and C-terminals in SEQ ID NO:3, and the resultant mixture was volumed up to 100 μl with sterilized distilled-water. The mixture was in usual manner successively incubated at 94° C. for one min, at 55° C. for 2 min, and at 72° C. for 3 min, and the successive incubation was repeated 40 cycles. The resultant PCR product was cleaved with Bam HI and Eco RI as a restriction enzyme to obtain a Bam HI-Echo RI DNA fragment.

To an adequate amount of sterilized distilled-water were added 100 ng of the fragment, 10 ng of "pGEX-2T", a plasmid vector commercialized by Pharmacia LKB, Uppsala, Sweden, which had been cleaved with Bam HI and Echo RI as a restriction enzyme, an adequate amount of T4 DNA ligase, and 10 mM ATP in an amount of which gives the final concentration of one mM, followed by incubating the mixture solution at 16° C. for 18 hours. The recombinant DNA thus obtained was introduced into *Escherichia coli* DH5 strain (ATCC 53868) to obtain a transformant which was then inoculated into L-broth (pH 7.2) containing 50 μg/l of ampicillin, followed by the incubation at 37° C. for 18 hours and extracting the objective recombinant DNA by conventional SDS-alkali method.

Figure 2:
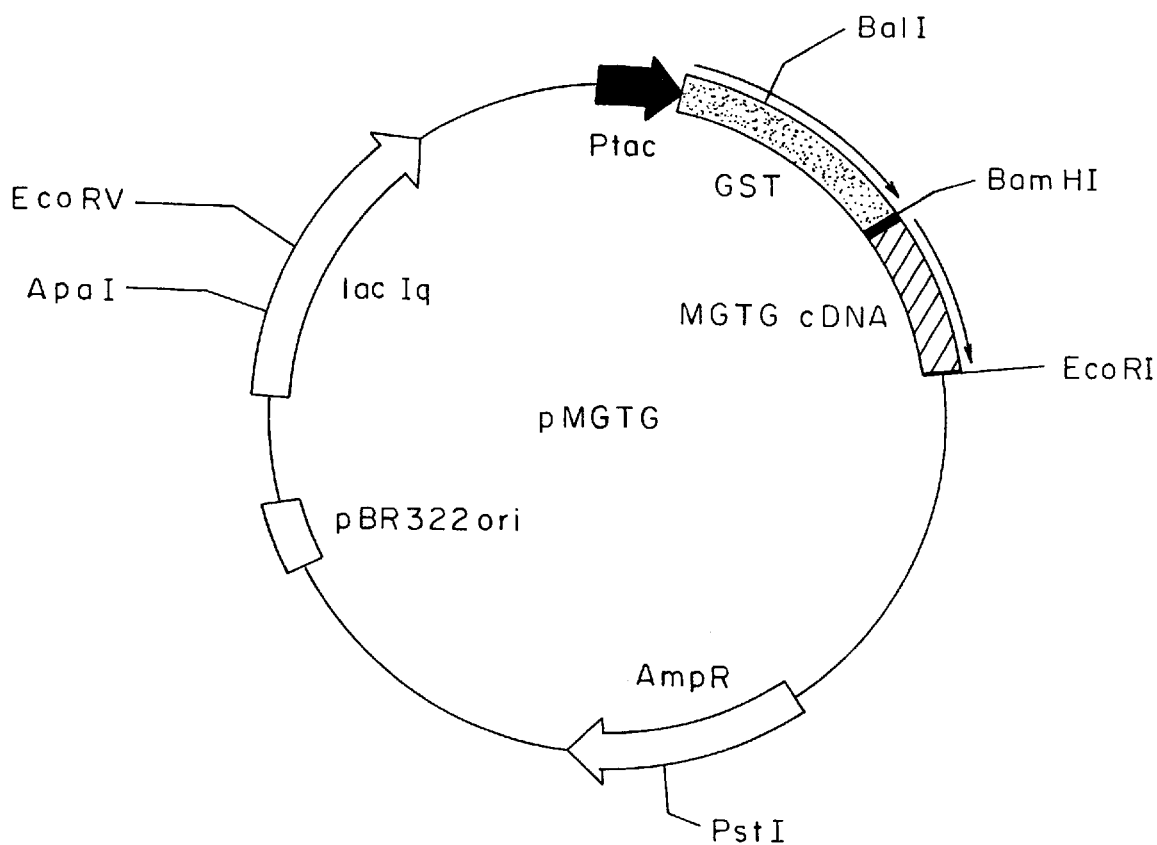
FIG. 2 is a structure of pMGTG-1, a recombinant DNA according to the present invention.
Figure 3:
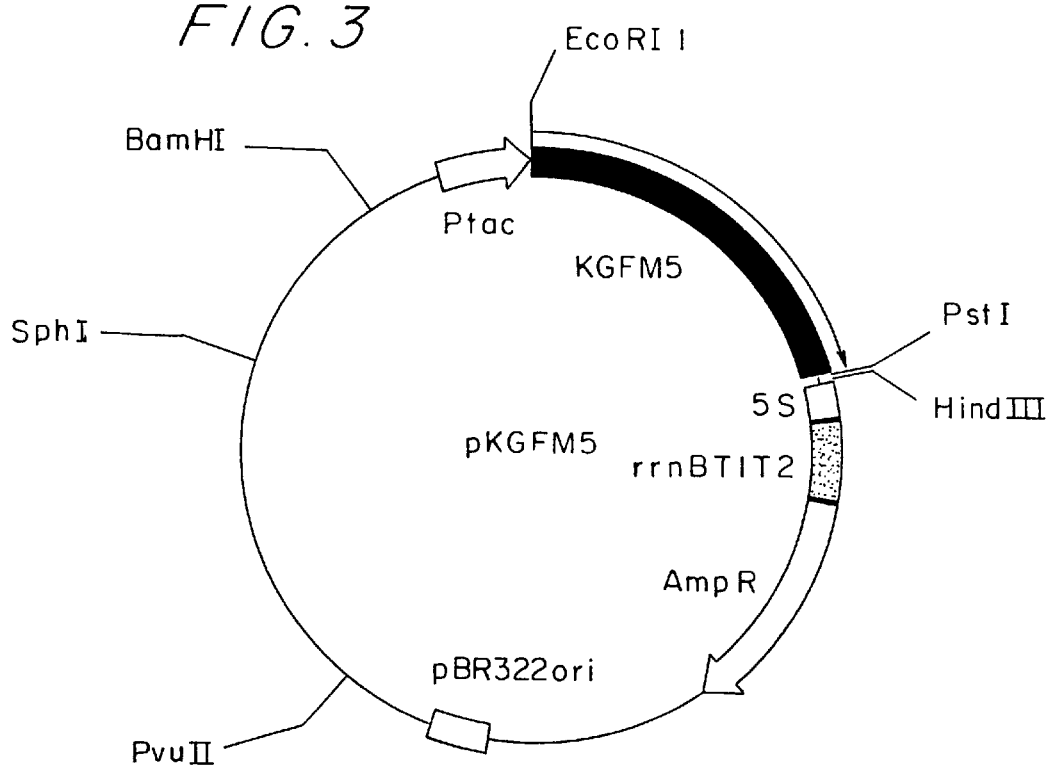
FIG. 3 is a structure of recombinant DNA pKGFM5.

The recombinant DNA was named "pMGTG-1" and analyzed for structure on the dideoxy chain termination method and revealing that, as is shown in FIG.2, in pMGTG-1, MGTG cDNA which has the base sequence of SEQ ID NO:2 is positioned in the downstream of the Tac promotor and the gene for glutathione S transferase.

EXAMPLE 2

Preparation of protein by transformant

A transformant obtained by the method in Example 1 was inoculated in L-broth (pH 7.2) containing 50 μg/ml of ampicillin, and cultured at 37° C. for 18 hours under shaking conditions. One v/v % of the proliferated transformants as a seed was inoculated into 18 L of a fresh preparation of the same medium, and cultured at 37° C. under aeration-agitation conditions until the absorbance at a wavelength of 650 nm ($A_{650}$) of the culture reached to about 0.6, followed by adding IPTG to the culture to give a concentration of one mM. Thereafter, the resultant culture was incubated for 5 hours and centrifuged to separate cells which were then suspended in a mixture solution (pH 7.3) containing 150 mM sodium chloride, 16 mM disodium hydrogen phosphate, and 4 mM sodium dihydrogen phosphate, treated in usual manner with ultrasonication, and centrifuged to remove cell debris to obtain a supernatant.

The supernatant was fed to a column packed with "GLU-TATHIONE SEPHAROSE 4B", a gel commercialized by Pharmacia LKB, Uppsala, Sweden, which had been equilibrated with 50 mM Tris-HCl buffer (pH 7.5) supplemented with 150 mM sodium chloride, and the column was washed with a fresh preparation of the same buffer and fed with 50 mM Tris-HCl buffer (pH 8.0) supplemented with 5 mM reducing glutathione to elute proteins. Fractions containing proteins were pooled, mixed with calcium chloride to give a concentration of 2.5 mM together with 1,000 units of thrombin, and incubated at 25° C. for 18 hours. The reaction mixture was fed to a column packed with "GLUTATHIONE SPEPHAROSE 4B", which had been equilibrated with 50 mM Tris-HCl buffer (pH 7.5) supplemented with 150 mM sodium chloride, followed by recovering non-adsorbed fractions. Thereafter, the fractions were pooled, concentrated, lyophilized to obtain a solid preparation containing the present protein with a specific activity of about $5 \times 10^5$ units/mg protein in a yield of about 3 mg per one L of the culture.

Similarly as in Experiment 2, the purified protein was studied on the physicochemical properties and revealing that it has a molecular weight of 19,000±5,000 daltons on gel filtration and SDS-PAGE, and a pI of 4.8±1.0 on chromato-focusing. The testing by the method in Experiment 2-4 revealed that the purified protein effectively induces the IFN-γ production by immunocompetent cells independently of the presence of concanavalin A (Con A), and strongly augments the cytotoxicity of killer cells. This is an evidence that the present protein can be prepared by the recombinant DNA technology.

EXAMPLE 3

Preparation of hybridoma M-1

EXAMPLE 3-1

Preparation of transformant KGFM5

To 0.5-ml reaction tube were added 8 μl of 25 mM magnesium chloride, 10 μl of 10×PCR buffer, one μl of 25 mM dNTP mix, one μl of 2.5 units/μl AmpliTaq DNA polymerase, one ng of a recombinant DNA containing a DNA encoding the present protein and having the base sequence in SEQ ID NO:2 which is prepared from a phage DNA clone according to the method described in Japanese Patent Application No.184,162/94, and an adequate amount of a sense primer and an anti-sense primer comprising the base sequences represented by 5'-GAGGAATTCTGGAGGAAGGTACCATGAACTTT GGC CGACTTC-3'(SEQ ID NO:8) and 5'-GCGAAAGCTTCTAACTTTGATGTAAG-3'(SEQ ID NO:9). The resultant mixture was volumed up to 100 μl with sterilized distilled-water, and successively incubated at 94° C. for one min, at 43° C. for one min, 72° C. for one min, at 60 for one min, and at 70° C. for one min. The successive incubation was repeated 37 cycles to effect polymerase chain reaction (PCR) to make restriction sites of Eco RI and Hind III at the 5'- and 3'-termini respectively.

Ten ng of the resultant PCR product, "pCR-Script SK(+)" commercialized by Stratagene Cloning Systems, California, USA, was in usual manner ligated with DNA ligase to obtain a recombinant DNA which was then transformed by introducing it into "XL-1 Blue MRF'Kan", a microorganism of the species *Escherichia coli* commercialized by Stratagene Cloning Systems, California, USA. The transformant was inoculated into L-broth (pH 7.2) containing 50 μg/ml of ampicillin, and cultured at 37° C. for 18 hours under shaking conditions. The resultant culture was centrifuged to obtain transformants, and from which a recombinant DNA was isolated by applying conventional SDS-alkali method. A portion of the recombinant DNA was provided and analyzed on the dideoxy method and revealing that the recombinant DNA was coupled with the DNA having the base sequence in SEQ ID NO:2, and the material DNA was correctly amplified by the PCR.

The remaining recombinant DNAs were in usual manner cleaved with Eco RI and Hind III as a restriction enzyme. By using "DNA Ligation Kit Version 2", a DNA ligation kit commercialized by Takara Shuzo Co., Ltd., Tokyo, Japan, 0.1 μg of the resultant Eco RI-Hind III DNA fragment and 10 ng of "pKK223-3", a plasmid vector commercialized by Pharmacia LKB, Uppsala, Sweden, which had been previously cleaved with the above restriction enzymes, were ligated by reacting them at 16° C. for 30 min to obtain "pKGFM5", a replicable recombinant DNA. With competent cell method, *Escherichia coli* Y1090 strain (ATCC 37197) was transformed by the recombinant DNA pKGFM5, and the formed transformant "KGFM5" was inoculated into L-broth (pH 7.2) containing 50 μg/ml ampicillin, and cultured at 37° C. for 18 hours under shaking conditions. The resultant culture was centrifuged to collect transformants, and a portion of which was treated with the SDS-alkali method to extract the objective recombinant DNA pKGFM5. The analysis on the dideoxy method revealed that KGFM5 cDNA having the base sequence in SEQ ID NO:2 was coupled to the site of the downstream of the Tac promotor.

EXAMPLE 3-2

Production of protein by transformant FGFM5

L-Broth (pH 7.2) containing 50 μg/ml was sterilized by an autoclave and cooled to 37° C. which was then inoculated with transformant KGFM5 in Example 3-1, and incubated at the same temperature for 18 hours under shaking conditions to obtain a seed culture. Eighteen L of a fresh preparation of the same L-broth was placed in a 20-L jar fermenter, sterilized similarly as above, and cooled to 37° C., which was then inoculated with one v/v % of the seed culture, and incubated at the same temperature for 8 hours under aeration-agitation conditions. The resultant culture was centrifuged to obtain cells which were then suspended in a mixture solution (pH 7.3) containing 150 mM sodium chloride and 16 mM disodium hydrogen phosphate, and 4 mM sodium dihydrogen phosphate, disrupted by ultrasonic and centrifuged to remove cell debris, followed by recovering the resultant supernatant.

Ammonium sulfate was added to and completely dissolved in the supernatant up to give a concentration of 40 w/v % under ice-chilling conditions, allowed to stand, and centrifuged to obtain a supernatant. The supernatant thus obtained was mixed with ammonium sulfate up to give a concentration of 85 w/v %, stirred at 4° C. for 25 hours and centrifuged to obtain a sediment containing the present protein which was then dissolved in 150 mM phosphate buffer (pH 6.6) containing 1.5.M ammonium sulfate. The resultant solution was fed to a column packed with "PHENYL SEPHAROSE", a product commercialized by Pharmacia LKB, Uppsala, Sweden, which had been previously equilibrated with 10 mM phosphate buffer (pH 6.6) containing 1.5 M ammonium sulfate. The column was washed with a fresh preparation of the same buffer, and fed with a linear gradient ranging from 1.5 M to 0 M ammonium sulfate in 10 mM phosphate buffer (pH 6.6).

Fractions eluted at about 0.9 M ammonium sulfate were pooled and concentrated with a membrane filter, and the concentrate was dialyzed against 10 mM phosphate buffer (pH 6.5) at 4° C. for 18 hours. The dialyzed solution was fed to a column packed with "DEAE 5PW", a product commercialized by Tosoh Corporation, Tokyo, Japan, which had been previously equilibrated with 10 mM phosphate buffer (pH 6.5), and the column was washed with a fresh preparation of the same buffer and fed with a linear gradient ranging from 0 M to 0.2 M in 10 mM phosphate buffer (pH 6.5), followed by collecting fractions eluted at about 0.1 M sodium chloride.

The fractions were pooled and concentrated, and the concentrate thus obtained was fed to a column packed with "SUPER-DEX 75", a product of Pharmacia LKB Uppsala, Sweden, which had been previously equilibrated with phosphate buffer and fed with a fresh preparation of the same phosphate buffer to elute fractions corresponding to a molecular weight of about 19,000 daltons. Thus, an aqueous solution containing about 4.7 mg of a purified protein. The total yield of the protein in this purification steps was about 26%.

The analysis according to the method as disclosed in Japanese Patent Application No.184,162/94 revealed that the purified protein has the following physicochemical properties. The analysis of the purified protein on sodium dodecyl sulfate polyacrylamide gel electrophoresis (SDS-PAGE) under non-reducing conditions revealed that it showed a main protein band which corresponds to a molecular weight of 19,000±5,000 daltons and has an activity of inducing IFN-γ, and had an isoelectric point of 4.8±1.0 on chromatofocusing. Two peptide fragments obtained after trypsinization had amino acid sequences in corresponding to amino acid residues 26–43 and 79–103 of SEQ ID NO:2 respectively.

EXAMPLE 3-3

Preparation of hybridoma M-1

A purified protein obtained by the method in Example 3-2 and complete Freund adjuvant were intraperitoneally injected to 10-week-old SD rats at a dose of 20 μg/rat. Thereafter, the rats were injected 2 times with the same dose at an interval of 2 weeks, and intravenously injected with the same dose one week after the final injection. On 3 days after the intravenous injection, the spleens were extracted and dispersed to obtain a cell suspension.

The spleen cells and SP2/0-Ag14 cells (ATCC CRL 1581) derived from mouse myeloma were suspended in serum-free RPMI 1640 (pH 7.2) to give cell densities of $3 \times 10^4$ cells/ml and $1 \times 10^4$ cells/ml, respectively, and the cells suspension was centrifuged to collect the resultant precipitate. One ml of serum-free RPMI 1640 medium (pH 7.2) containing 50 w/v % polyethylene glycol with an average molecular weight of 1,500 daltons was added to the precipitate drop by drop over one min, and the suspension was incubated at 37° C. for one min, and to which was added drop by drop serum-free RPMI 1640 medium (pH 7.2) up to give a total volume of 50 ml. The mixture was centrifuged to collect sediment which was then suspended in HAT medium. The suspension was distributed into 96-well microplate in an amount of 200 μl/well, and incubated at 37° C. for one week, followed by selecting hybridomas. The reactivity between a purified protein obtained by the method in Example 3-2 and the antibody secreted in the culture supernatant in each well was studied on enzyme immunoassay, followed by selecting hybridomas which formed antibody that reacted with the purified protein. According to conventional manner, the hybridoma was repeatedly subjected to the limited dilution to obtain hybridoma M-1 which forms the present monoclonal antibody.

EXAMPLE 4

Preparation of monoclonal antibody M-1mAb and analysis on Western blot technique

EXAMPLE 4-1

Preparation of monoclonal antibody M-1mAb

Hybridoma M-1 obtained by the method in Example 3-3 was suspended in RPMI 1640 medium (pH 7.2) supplemented with 5 v/v % calf serum to give a cell density of about $1 \times 10^6$ cells/ml, and incubated at 37° C. under 5 v/v % $CO_2$ conditions while the culture was stepwisely scaling up. When the cell density reached to the prescribed level, $1 \times 10^7$ cells/rabbit of hybridoma M-1 was intraperitoneally injected into 5-week-old hamsters, which had been immunosuppressed with an anti-hamster thymus antibody prepared from rabbits and intraperitoneally injected with 0.5 ml/hamster of pristane, and fed for one week in usual manner.

The hamsters were collected their ascites which were then diluted with phosphate buffer by 3 times, mixed with ammonium sulfate to give a saturation degree of 50 w/v %, allowed to stand at 4° C. for 24 hours, and centrifuged. The resultant sediment was collected, dialyzed against 20 mM potassium dihydrogen phosphate (pH 6.7) at 4° C. overnight, and the dialyzed solution was fed to a column packed with hydroxyapatite which had been previously equilibrated with a fresh preparation of the same buffer. The column was fed with a linear gradient ranging from 20 mM to 300 mM in an aqueous potassium dihydrogen phosphate solution (pH 6.7) to obtain an aqueous solution containing the present monoclonal antibody M-1mAb. The yield was about 5 mg/hamster. Conventional analysis of the monoclonal antibody revealed that it is a class of IgM.

EXAMPLE 4-2

Analysis on Western blot technique

A mixture solution, consisting of 100 mg dithiothreitol, 0.5 ml of 10 w/v % aqueous SDS solution, one ml of glycerol, was mixed with a purified protein obtained by the method in Example 3-2, and the resultant mixture was incubated at 37° C. for one hour and subjected to SDS-PAGE. The resultant gel was in usual manner transferred to a nitrocellulose membrane which was then soaked in a culture supernatant of hybridoma M-1 for one hour, washed with 50 mM Tris-HCl buffer (pH 7.5) containing 0.05 v/v % tween 20 to remove excessive amount of antibody. The resultant nitrocellulose membrane was soaked for one hour in phosphate buffer containing an anti-rat immunoglobulin antibody which was prepared from rabbits and labeled with horseradish peroxidase, washed with 50 mM Tris-HCl buffer (pH 7.5) containing 0.05 v/v % tween 20, and soaked in 50 mM Tris-HCl buffer (pH 7.5) containing 0.005 v/v % hydrogen peroxide and 0.3 mg/ml diamino benzine to effect coloration.

As a control, a system, where a purified protein derived from mouse liver cell obtained by the method in Example 6 or a recombinant human interleukin 12 is used in place of the purified protein, is provided and treated similarly as above. The marker proteins used in this experiment were calf serum albumin (MW=67,000 daltons), ovalbumin (MW=45,000 daltons), carbonic anhydrolase (MW=30,000 daltons), trypsin inhibitor (MW=20,100 daltons) and α-lactalbumin (MW=14,400 daltons).

Figure 4:
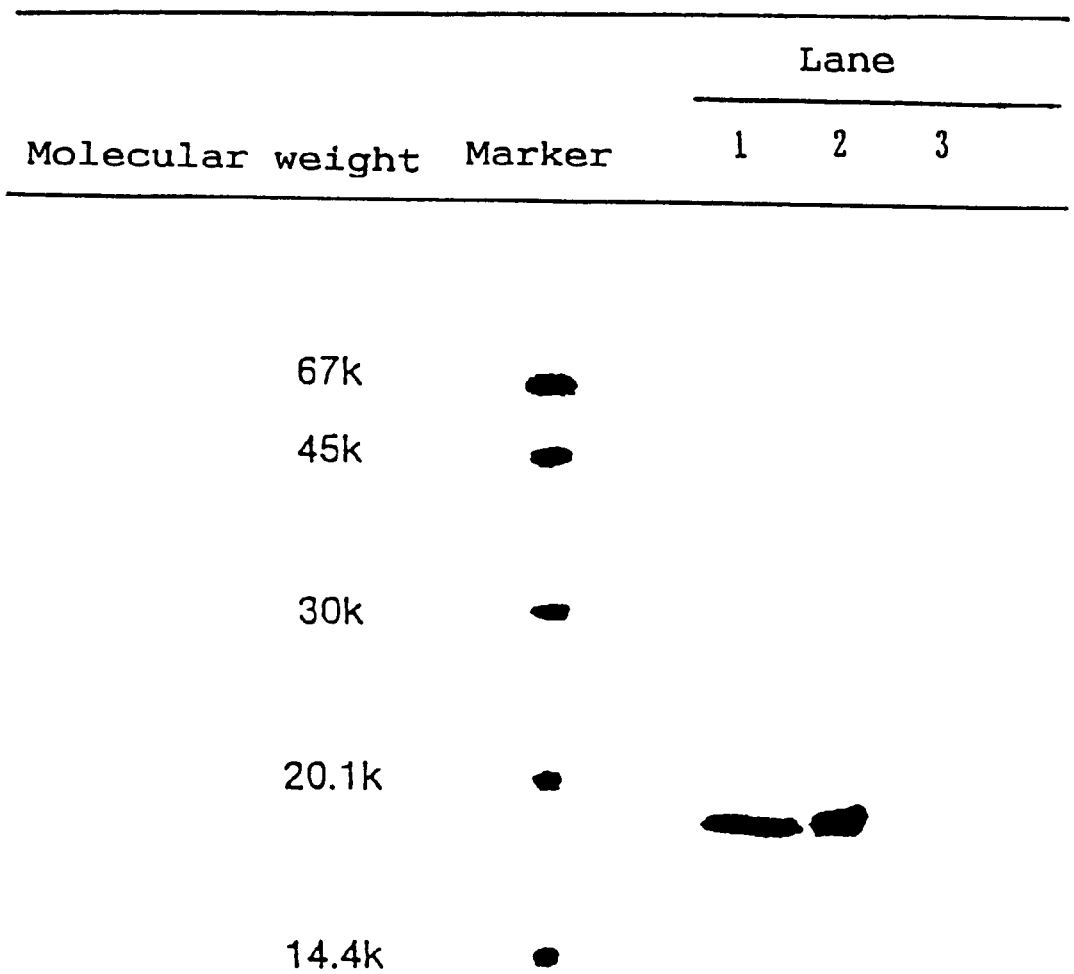
FIG. 4 is a figure of the reactivity of the present monoclonal antibody M-1mAb with a protein on Western blot technique.

As is shown in FIG. 4, the monoclonal antibody M-1mAb specifically reacted with the purified protein obtained by the method in Example 3-2 (lane 1), and the purified protein obtained by the method in Example 6 (lane 2). This indicates that the present monoclonal antibody specifically reacts with proteins having specific physicochemical properties independently of their preparations.

EXAMPLE 5

Purification of protein on immunoaffinity chromatography

EXAMPLE 5-1

Preparation of gel for immunoaffinity chromatography

Eighty mg of monoclonal antibody M-1mAb obtained by the method in Example 4-1 was weighed and dialyzed against 0.1 M borate buffer (pH 8.5) containing 0.5 M sodium chloride at 4° C. overnight. Four g of "CNBr-activated sepharose 4B", a product of Pharmacia LKB, Uppsala, Sweden, as a water-soluble carrier, was swelled in one mM aqueous chloric acid solution, and washed with a fresh preparation of the same aqueous solution and 0.1 M borate buffer (pH 8.5) containing 0.5 M sodium chloride in this order, admixed with about 10 ml of the above dialyzed aqueous solution of monoclonal antibody, and successively gently stirred at ambient temperature for 2 hours and at 4° C. overnight. The formed gel was first washed with one M aqueous ethanol amine solution (pH 8.0), then successively washed with 0.1 M borate buffer (pH 8.5) containing 0.5 M sodium chloride, and 0.1 M acetate buffer (pH 4.0) containing 0.5 M sodium chloride, and these washing steps were repeated 5 cycles. Finally, the resultant gel was washed with phosphate buffer to obtain a gel for immunoaffinity chromatography. Conventional analysis revealed that about 6 mg monoclonal antibody M-1mAb bound to one ml gel.

EXAMPLE 5-2

Purification of protein on immunoaffinity chromatography

Ten ml of the gel for immunoaffinity chromatography in Example 5-1 was injected into a plastic cylindrical column, and the column was washed with phosphate buffer and loaded with 10 ml of fractions eluted from phenyl sepharose column containing about 0.1 mg/ml of the present purified protein obtained by the method in Example 3-2. Thereafter, the column was washed with a fresh phosphate buffer and fed with 35 mM aqueous ethylamine solution (pH 10.8), followed by recovering fractions with IFN-γ inducing activity. The fractions were pooled, concentrated, and measured for IFN-γ inducing activity and protein content and revealing that a purified protein with a purity of at least 95% was obtained in a yield of nearly 100% to the material.

EXAMPLE 6

Purification of protein on immunoaffinity chromatography

Six hundred 8-week-old female mice were intraperitoneally injected with one mg/mouse of dead cells of Corynebacterium parvum strain (ATCC 11827) prepared by heating at 60° C. for one hour, fed in usual manner for 7 days, and intravenously injected with one μg/mouse of a purified lipopolysaccharide derived from *Escherichia coli*. One to 2 hours after the intravenous injection, the mice were sacrificed, collected blood form their hearts, extracted their livers, and disrupted with a homogenizer in 8-fold volumes of 50 mM phosphate buffer (pH 7.3) to effect extraction. The resultant extract was centrifuged at about 8,000 rpm for 20 min to obtain an about 9 L supernatant which was then mixed with 50 mM phosphate buffer (pH 7.3) containing saturated ammonium sulfate up to give a saturation degree of 45 w/v %, allowed to stand at 4° C. for 18 hours, and centrifuged at about 8,000 rpm for 30 min to obtain an about 19 L supernatant containing the present protein.

The supernatant thus obtained was fed to a column packed with about 4.6 L of "PHENYL SEPHAROSE", a product of Pharmacia LKB, Uppsala, Sweden, which had been previously equilibrated with 50 mM phosphate buffer (pH 7.3) containing one M ammonium sulfate, and the column was washed with a fresh preparation of the same buffer, and fed with a linear gradient of ammonium sulfate ranging from 1 M to 0.2 M in 50 mM phosphate buffer (pH 7.3) at an SV (space velocity) 0.57. About 4.8 L of fractions containing the present protein eluted at a concentration of about 0.8 M ammonium sulfate, was concentrated with a membrane, dialyzed against 20 mM phosphate buffer (pH 6.5) at 4° C. for 18 hours, and fed to a column packed with about 250 ml of "DEAE-SEPHAROSE", a product of Pharmacia LKB, Uppsala, Sweden. Thereafter, the column was washed with a fresh preparation of the same buffer and fed with 20 mM phosphate buffer (pH 6.5) containing sodium chloride ranging from 0 M to 0.2 M at an SV 1.2 to elute the present protein at about 0.13 M sodium chloride.

An about 260 ml eluate containing the present protein was collected, concentrated and purified similarly as in Example 5 to obtain a purified protein with a purity of at least 95% in a yield of nearly 100% to the material.

EXAMPLE 7

Detection of protein on enzyme immunoassay

According to conventional method, rabbits were immunized with a purified protein obtained by the method in Example 3-2, and the rabbits were collected their blood, and from which IgG antibody was isolated, dissolved in phosphate buffer to give 20 μg/ml. One hundred μl aliquots of the resultant solution were distributed into 96-well microplates which were then incubated at ambient temperature for 3 hours, followed by removing supernatants containing IgG in the wells, adding to the wells 100 μl/well of phosphate buffer containing one w/v % calf serum albumin, and allowing the microplates to stand at 4° C. overnight.

From the microplates supernatants were removed, and the microplates were washed with phosphate buffer containing 0.05 v/v % tween 20. A purified protein obtained by the method in Example 3-2 was diluted with phosphate buffer containing 0.5 w/v % calf serum albumin to give a prescribed concentration, and the diluted solution was added to the wells in a volume of 100 μl/well, followed by the reaction at ambient temperature for 2 hours under shaking conditions. The wells were washed with phosphate buffer containing 0.05 v/v % tween 20, mixed with 100 μl/well of monoclonal antibody M-1mAb labeled with biotin, followed by the reaction at ambient temperature for 2 hours under shaking conditions. Thereafter, the wells were washed with phosphate buffer containing 0.05 v/v % tween 20, and 100 μl/well of a complex of horseradish peroxidase and streptoavidin, and subjected to immunological reaction at ambient temperature for 2 hours under shaking conditions. Thereafter, the wells were washed with phosphate buffer containing 0.05 v/v % tween 20, and the activity of horseradish peroxidase coupled to the purified protein was measured based on the absorbance at a wavelength of 492 nm. The results were in Table 2.

TABLE 2

| Concentration of protein (pg/ml) | Absorbance at wavelength of 492 nm (mean value of triplicate) | Relative error (%) |
| --- | --- | --- |
| 2,000 | 1.490 ± 0.030 | 2.0 |
| 1,000 | 0.723 ± 0.007 | 1.0 |
| 500 | 0.370 ± 0.020 | 5.4 |
| 250 | 0.210 ± 0.010 | 4.8 |
| 100 | 0.090 ± 0.010 | 11.1 |
| 50 | 0.054 ± 0.004 | 6.7 |
| 0 | 0.017 ± 0.003 | 17.6 |

As is evident from Table 2, the present detection method can accurately detect at least about 50–2,000 μg/ml of the present protein.

EXAMPLE 8

Detection of protein on radioimmunoassay

According to conventional method, rabbits were immunized with a purified protein obtained by the method in Example 3-2 and collected their blood, and from which IgG antibody was isolated. The antibody thus obtained was in usual manner allowed to adsorb on polystyrene beads for radioimmunoassay, and the resultant beads were allowed to stand at 4° C. overnight to obtain an immobilized antibody.

The immobilized antibody, a bead with the antibody, was placed in a test tube, mixed with 0.2 ml of a purified protein, obtained by the method in Example 3-2, which had been diluted with phosphate buffer containing 0.5 w/v % calf serum albumin, and allowed to stand at 4° C. for 4 hours. Thereafter, the resultant bead was washed with phosphate buffer containing 0.05 v/v % tween 20 and 0.5 w/v % calf serum albumin, contacted with 0.2 ml ($1 \times 10^5$ cpm) of monoclonal antibody M-1mAb, obtained by the method in Example 4-1, which had been previously labeled with $^{125}$I, and allowed to stand at 4° C. overnight. From the system, an excessive amount of labeled antibody was removed, and the resultant bead was washed with phosphate buffer containing 0.05 v/v % tween 20 and 0.5 w/v % calf serum albumin, followed by counting the radioactivity of the bead. The results were in Table 3.

TABLE 3

| Concentration of protein (pg/ml) | Count (cpm) (mean value of triplicate) | Relative error (%) |
| --- | --- | --- |
| 1,150 | 15,900 ± 700 | 4.4 |
| 575 | 9,100 ± 200 | 2.2 |
| 288 | 4,700 ± 200 | 4.3 |
| 144 | 2,300 ± 50 | 2.2 |
| 72 | 1,217 ± 4 | 0.3 |
| 0 | 159 ± 4 | 2.6 |

As is evident from Table 3, the detection method can accurately detect at least about 100–1,200 μg/ml of the protein.

In summary the present invention is based on the finding of a novel protein which induces the IFN-γ production by immunocompetent cells. The present protein is generally a substance with a partially or totally revealed amino acid sequence which has a stable activity of inducing IFN-γ production by immunocompetent cells. Therefore, the present protein is widely used as an IFN-γ inducer for the IFN-γ production by the cell culture method and as a therapeutic and/or prophylactic agent in general for IFN-γ susceptive diseases such as viral diseases, malignant tumors and immunopathies.

The present protein has a strong IFN-γ inducibility so that it can induce the desired amount of IFN-γ production with only a relatively small amount. The protein dose not cause serious side effects even when administered to in a relatively large amount because of its extremely low toxicity. Therefore, the present protein has an advantage that it quickly induces the desired amount of IFN-γ production without strictly controlling the dose. The present protein has an outstanding activity of increasing the cytotoxicity of killer cells and inducing a strong activity on the therapeutic effect and/or the reduction of side effects in the treatment of adoptive immunotherapy for malignant tumors including solid carcinomas such as lung cancer, renal cancer and breast cancer.

The present protein with these useful properties can be obtained in a desired amount by using the present DNA encoding the protein.

The present invention is a significant invention that exerts such a remarkable effect and gives a great contribution to this field.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. An isolated DNA fragment obtainable from a DNA molecule of SEQ ID NO:1 and capable of being used as a probe or as a primer, wherein said DNA molecule encodes a polypeptide capable of inducing IFN-γ production by immunocompetent cells and has a molecular weight of about 19,000±5,000 daltons on sodium dodecyl sulfate polyacrylamide gel electrophoresis (SDS-PAGE) and an isoelectric point of about 4.8±1.0 on chromatofocusing.

2. The isolated DNA fragment according to claim 1, which consists of a sequence corresponding to nucleotides 76 to 129 or nucleotides 235 to 309 of SEQ ID NO:1.

3. An isolated collection of DNA fragments obtainable from a DNA molecule of SEQ ID NO:1 and capable of being used as probes or as primers, wherein said DNA molecule encodes a polypeptide capable of inducing IFN-γ production by immunocompetent cells and has a molecular weight of about 19,000±5,000 daltons on sodium dodecyl sulfate polyacrylamide gel electrophoresis (SDS-PAGE) and an isoelectric point of about 4.8±1.0 on chromatofocusing.

4. The isolated collection of DNA fragments according to claim 3, wherein two of said DNA fragments of the collection consists of a sequence corresponding to nucleotides 26 to 43 or nucleotides 79 to 103 of SEQ ID NO:1.

5. An isolated DNA molecule which comprises a nucleotide sequence encoding a polypeptide capable of inducing IFN-γ production by immunocompetent cells, wherein said polypeptide is a variant of the polypeptide of SEQ ID NO:2, in which one or more amino acid residues are deleted from the N-terminus or one amino acid is replaced with a different amino acid residue, but which retains the capability of the polypeptide of SEQ ID NO:2 to induce IFN-γ production by immunocompetent cells.

6. The isolated DNA molecule according to claim 5, wherein said polypeptide encoded by said nucleotide sequence has the following physico-chemical properties:
   (1) Molecular weight 19,000±5,000 daltons on gel filtration and sodium dodecyl sulfate polyacrylamide gel electrophoresis (SDS-PAGE);
   (2) Isoelectric point (pI) 4.8±1.0 on chromatofocusing;
   (3) Partial amino acid sequence Possessing the partial amino acid sequence of SEQ ID NOs:1 and 2; and
   (4) Biological activity Inducing interferon-γ production by immunocompetent cells.

7. A replicable vector comprising the DNA molecule according to claim 5.

8. The replicable vector according to claim 7, wherein the vector is pGEX-2T plasmid.

9. A host cell transformed with the replicable vector of claim 8.

10. The transformed host cell according to claim 9, wherein the host cell is *Escherichia coli*.

11. A process for preparing an IFN-γ-inducing polypeptide, comprising the steps of:
   culturing a host cell transformed with the replicable vector of claim 7 in a nutrient medium and expressing the IFN-γ-inducing polypeptide; and
   recovering the expressed IFN-γ-inducing polypeptide.

* * * * *

UNITED STATES PATENT AND TRADEMARK OFFICE
CERTIFICATE OF CORRECTION

PATENT NO. : 6,277,598 B1  Page 1 of 1
DATED : August 21, 2001
INVENTOR(S) : Haruki Okamura et al.

It is certified that error appears in the above-identified patent and that said Letters Patent is hereby corrected as shown below:

Title page,
Item [54], Title, "DNA MOLECULE ENCODING INTERFERON-GAMMA (IFN-$\lambda$) INDUCING FACTOR (IGIF, IL-18) AND DNA FRAGMENT THEREOF" and insert therefor -- DNA MOLECULE ENCODING INTERFERON-GAMMA (IFN-$\gamma$) INDUCING FACTOR (IGIF, IL-18) AND DNA FRAGMENT THEREOF --.

Signed and Sealed this

Fifth Day of March, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 471 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..471
       (D) OTHER INFORMATION:/note= Xaa in position 70 is Met or Thr (xi) SEQUENCE DESCRIPTION: SEQ ID NO:1:

```
AAC TTT GGC CGA CTT CAC TGT ACA ACC GCA GTA ATA CGG AAT ATA AAT        48
Asn Phe Gly Arg Leu His Cys Thr Thr Ala Val Ile Arg Asn Ile Asn
 1               5                  10                  15

GAC CAA GTT CTC TTC GTT GAC AAA AGA CAG CCT GTG TTC GAG GAT ATG        96
Asp Gln Val Leu Phe Val Asp Lys Arg Gln Pro Val Phe Glu Asp Met
                20                  25                  30

ACT GAT ATT GAT CAA AGT GCC AGT GAA CCC CAG ACC AGA CTG ATA ATA       144
Thr Asp Ile Asp Gln Ser Ala Ser Glu Pro Gln Thr Arg Leu Ile Ile
            35                  40                  45

TAC ATG TAC AAA GAC AGT GAA GTA AGA GGA CTG GCT GTG ACC CTC TCT       192
Tyr Met Tyr Lys Asp Ser Glu Val Arg Gly Leu Ala Val Thr Leu Ser
 50                  55                  60

GTG AAG GAT AGT AAA AYG TCT ACC CTC TCC TGT AAG AAC AAG ATC ATT       240
Val Lys Asp Ser Lys Xaa Ser Thr Leu Ser Cys Lys Asn Lys Ile Ile
 65                  70                  75                  80

TCC TTT GAG GAA ATG GAT CCA CCT GAA AAT ATT GAT GAT ATA CAA AGT       288
Ser Phe Glu Glu Met Asp Pro Pro Glu Asn Ile Asp Asp Ile Gln Ser
                85                  90                  95

GAT CTC ATA TTC TTT CAG AAA CGT GTT CCA GGA CAC AAC AAG ATG GAG       336
Asp Leu Ile Phe Phe Gln Lys Arg Val Pro Gly His Asn Lys Met Glu
            100                 105                 110

TTT GAA TCT TCA CTG TAT GAA GGA CAC TTT CTT GCT TGC CAA AAG GAA       384
Phe Glu Ser Ser Leu Tyr Glu Gly His Phe Leu Ala Cys Gln Lys Glu
        115                 120                 125

GAT GAT GCT TTC AAA CTC ATT CTG AAA AAA AAG GAT GAA AAT GGG GAT       432
Asp Asp Ala Phe Lys Leu Ile Leu Lys Lys Lys Asp Glu Asn Gly Asp
130                 135                 140

AAA TCT GTA ATG TTC ACT CTC ACT AAC TTA CAT CAA AGT                   471
Lys Ser Val Met Phe Thr Leu Thr Asn Leu His Gln Ser
145                 150                 155
```

(2) INFORMATION FOR SEQ ID NO:2:

(i) SEQUENCE CHARACTERISTICS:
       (A) LENGTH: 157 amino acids
       (B) TYPE: amino acid
       (D) TOPOLOGY: linear (ii) MOLECULE TYPE: protein (xi) SEQUENCE DESCRIPTION: SEQ ID NO:2:

Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Xaa Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
130                 135                 140

Lys Ser Val Met Phe Thr Leu Thr Asn Leu His Gln Ser
145                 150                 155

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:3:

ATRTCRTCDA TRTTYTCNGG                                          20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:4:

TTYGARGAYA TGACNGAYAT                                          20

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:5:

```
TTYGARGARA TGGAYCC                                                          17
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CGAGGGATCG AACTTTGGCC GACTTC                                                26
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CGAGGAATTC CTAACTTTGA TGTAAG                                                26
```

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GAGGAATTCT GGAGGAAGGT ACCATGAACT TTGGCCGACT TC                              42
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GCGAAAGCTT CTAACTTTGA TGTAAG                                                26
```